US011801340B2

(12) United States Patent
Antonio et al.

(10) Patent No.: US 11,801,340 B2
(45) Date of Patent: *Oct. 31, 2023

(54) INFUSION SET COMPONENT WITH MODULAR FLUID CHANNEL ELEMENT

(71) Applicant: MEDTRONIC MINIMED, INC., Northridge, CA (US)

(72) Inventors: David Christopher Antonio, Pasadena, CA (US); Sumona Nag Adhya, Los Angeles, CA (US); Jose J. Ruelas, San Fernando, CA (US); Eric Allan Larson, Simi Valley, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 749 days.

This patent is subject to a terminal disclaimer.

(21) Appl. No.: 16/849,918

(22) Filed: Apr. 15, 2020

(65) Prior Publication Data

US 2020/0238000 A1    Jul. 30, 2020

Related U.S. Application Data

(62) Division of application No. 15/434,876, filed on Feb. 16, 2017, now Pat. No. 10,661,006, which is a (Continued)

(51) Int. Cl.
*A61M 5/14* (2006.01)
*A61B 5/00* (2006.01)
(Continued)

(52) U.S. Cl.
CPC ......... *A61M 5/1413* (2013.01); *A61B 5/0002* (2013.01); *A61B 5/1486* (2013.01); *A61B 5/14532* (2013.01); *A61B 5/4839* (2013.01); *A61M 5/1452* (2013.01); *A61M 5/14244* (2013.01); *A61M 5/158* (2013.01);
(Continued)

(58) Field of Classification Search
CPC ............ A61M 5/14248; A61M 5/1413; A61M 5/158; A61M 2005/1581; A61M 2005/1587; A61M 2005/1586; A61M 2025/028
See application file for complete search history.

(56) References Cited

U.S. PATENT DOCUMENTS 4,755,173 A   7/1988 Konopka et al.
5,391,250 A   2/1995 Cheney, II et al.
(Continued)

FOREIGN PATENT DOCUMENTS

WO   WO2009/102355 A2   8/2009

*Primary Examiner* — Nathan R Price
*Assistant Examiner* — Anh Bui
(74) *Attorney, Agent, or Firm* — Foley & Lardner LLP

(57) ABSTRACT

A fluid channel module for an infusion set component of a fluid infusion device that delivers a fluid to a patient includes a body section comprising coupling features to mate with a base of the infusion set component. The fluid channel module includes an interior fluid flow channel formed within the body section to receive the fluid from the fluid infusion device. The fluid channel module includes a conduit having a first end in fluid communication with the interior fluid flow channel, and having a second end to deliver the fluid to the patient.

19 Claims, 18 Drawing Sheets

Related U.S. Application Data division of application No. 13/463,637, filed on May 3, 2012, now Pat. No. 9,610,401.

(60) Provisional application No. 61/586,647, filed on Jan. 13, 2012.

(51) Int. Cl.
*A61B 5/145* (2006.01)
*A61M 5/142* (2006.01)
*A61M 5/158* (2006.01)
*A61B 5/1486* (2006.01)
*A61M 5/145* (2006.01)

(52) U.S. Cl.
CPC .. *A61B 5/14865* (2013.01); *A61M 2005/1581* (2013.01); *A61M 2005/1586* (2013.01); *A61M 2005/1587* (2013.01); *A61M 2205/3592* (2013.01)

(56) References Cited

U.S. PATENT DOCUMENTS

| | | | |
|---|---|---|---|
| 5,485,408 | A | 1/1996 | Blomquist |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,056,718 | A | 5/2000 | Funderburk et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,485,465 | B2 | 11/2002 | Moberg et al. |
| 6,544,212 | B2 | 4/2003 | Galley et al. |
| 6,554,798 | B1 | 4/2003 | Mann et al. |
| 6,558,351 | B1 * | 5/2003 | Steil ................. A61M 5/14244 604/522 |
| 6,591,876 | B2 | 7/2003 | Safabash |
| 6,641,533 | B2 | 11/2003 | Causey, III et al. |
| 6,736,797 | B1 | 5/2004 | Larsen et al. |
| 6,749,587 | B2 | 6/2004 | Flaherty |
| 6,752,787 | B1 | 6/2004 | Causey, III et al. |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 6,932,584 | B2 | 8/2005 | Gray et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,621,893 | B2 | 11/2009 | Moberg et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,905,868 | B2 | 3/2011 | Moberg et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 9,610,401 | B2 * | 4/2017 | Antonio ............ A61M 5/14244 |
| 10,661,006 | B2 * | 5/2020 | Antonio ............ A61B 5/14532 |
| 2002/0137997 | A1 | 9/2002 | Mastrototaro et al. |
| 2005/0113761 | A1 * | 5/2005 | Faust ................ A61M 39/0247 604/180 |
| 2007/0123819 | A1 | 5/2007 | Mernoe et al. |
| 2009/0299299 | A1 | 12/2009 | Lynch et al. |
| 2010/0160861 | A1 | 6/2010 | Causey, III et al. |
| 2014/0350485 | A1 | 11/2014 | Sonderegger et al. |

\* cited by examiner

INFUSION SET COMPONENT WITH MODULAR FLUID CHANNEL ELEMENT

CROSS-REFERENCE TO RELATED APPLICATION(S)

This application is a divisional of U.S. patent application Ser. No. 15/434,876 filed on Feb. 16, 2017, which is a divisional of U.S. patent application Ser. No. 13/463,637 filed on May 3, 2012 issued as U.S. Pat. No. 9,610,401, which claims the benefit of U.S. Provisional Patent Application No. 61/586,647, filed Jan. 13, 2012. The relevant content of each of the above applications is incorporated by reference herein.

TECHNICAL FIELD

Embodiments of the subject matter described herein relate generally to fluid infusion devices, such as insulin pumps and insulin injection ports. More particularly, embodiments of the subject matter relate to an infusion set component having a physically distinct and modular fluid channel element.

BACKGROUND

Portable medical devices are useful for patients that have conditions that must be monitored on a continuous or frequent basis. For example, diabetics are usually required to modify and monitor their daily lifestyle to keep their blood glucose (BG) in balance. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly.

The prior art includes a number of fluid infusion devices and insulin pump systems that are designed to deliver accurate and measured doses of insulin via infusion sets (an infusion set delivers the insulin through a small diameter tube that terminates at, e.g., a cannula inserted under the patient's skin). In lieu of a syringe, the patient can simply activate the insulin pump to administer an insulin bolus as needed, for example, in response to the patient's high BG level.

A typical infusion pump includes a housing, which encloses a pump drive system, a fluid containment assembly, an electronics system, and a power supply. The pump drive system typically includes a small motor (DC, stepper, solenoid, or other varieties) and drive train components such as gears, screws, and levers that convert rotational motor motion to a translational displacement of a stopper in a reservoir. The fluid containment assembly typically includes the reservoir with the stopper, tubing, and a catheter or infusion set to create a fluid path for carrying medication from the reservoir to the body of a user. The electronics system regulates power from the power supply to the motor. The electronics system may include programmable controls to operate the motor continuously or at periodic intervals to obtain a closely controlled and accurate delivery of the medication over an extended period.

The prior art also includes a variety of physiological characteristic (or analyte) sensors that are designed to measure an analyte of a patient. For example, continuous glucose sensors employ a subcutaneous glucose sensor technology that facilitates ongoing monitoring of blood glucose levels. Continuous glucose sensors may utilize wireless data communication techniques to transmit data indicative of the blood glucose levels to a portable infusion pump, a glucose monitor device, and/or other receiving devices. Thus, in a typical insulin pump system, the patient might wear both an infusion set (for the delivery of insulin) and a glucose sensor-transmitter.

BRIEF SUMMARY

The following description presents an exemplary embodiment of an infusion set component for a fluid infusion device that delivers fluid to a patient. The infusion set component includes a base and a fluid channel module coupled to the base. The base includes an attachment feature to accommodate removable coupling with a fluid tubing connector of the fluid infusion device, and a cavity formed therein to receive and maintain the fluid channel module. The fluid channel module includes an interior fluid flow channel to receive fluid from the fluid tubing connector. The fluid channel module also includes a conduit in fluid communication with the interior fluid flow channel to deliver fluid from the interior fluid flow channel. The interior fluid flow channel and the conduit cooperate to form a fluid flow path.

Also provided is an exemplary embodiment of a fluid channel module for an infusion set component of a fluid infusion device that delivers a fluid to a patient. The fluid channel module includes a body section having coupling features to mate with a base of the infusion set component. The fluid channel module also includes an interior fluid flow channel formed within the body section to receive the fluid from the fluid infusion device, and a conduit having a first end in fluid communication with the interior fluid flow channel, and having a second end to deliver the fluid to the patient.

Also provided is an exemplary embodiment of an infusion set component for a fluid infusion device that delivers a fluid to a patient using either a first fluid channel module or a second fluid channel module. The infusion set component includes a base body section, a fluid channel module interface formed in the base body section, and a sensor interface formed in the base body section. The fluid channel module interface has first universal coupling features that mate with corresponding second universal coupling features of the first fluid channel module and with corresponding third universal coupling features of the second fluid channel module. The sensor interface accommodates a sensor to facilitate sensing of an analyte of the patient.

An exemplary embodiment of a fluid infusion port component to accommodate delivery of fluid to a patient is also provided. The fluid infusion port component includes a base and a fluid channel module coupled to the base. The base has first universal coupling features that mate with corresponding second universal coupling features of the fluid channel module. The fluid channel module has an interior fluid flow channel having an inlet, along with a septum positioned at the inlet. The septum is pierced by a fluid delivery needle to accommodate delivery of fluid into the interior fluid flow channel. The septum seals the inlet when the fluid delivery needle is removed from the septum. The fluid channel module also includes a conduit in fluid communication with the interior fluid flow channel to deliver fluid from the interior fluid flow channel. The interior fluid flow channel and the conduit cooperate to form a fluid flow path.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
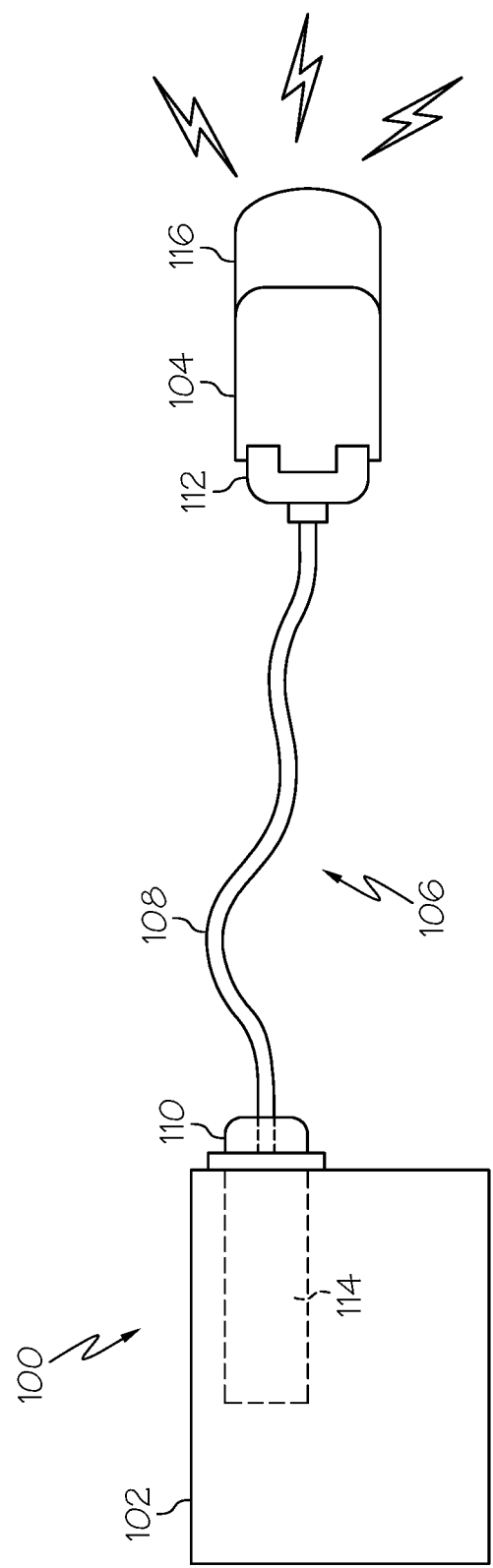
FIG. 1 is a schematic plan view of an exemplary embodiment of a fluid infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The subject matter described here relates to a fluid infusion device of the type used to treat a medical condition of a patient. The infusion device is used for infusing fluid into the body of a user. The non-limiting examples described below relate to a medical device used to treat diabetes (for example, an insulin pump, an injection port, or other type of insulin delivery system), although embodiments of the disclosed subject matter are not so limited. Accordingly, the infused fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like.

For the sake of brevity, conventional features and technologies related to infusion system operation, insulin pump and/or infusion set operation, blood glucose sensing and monitoring, sensor signal processing, and other functional aspects of the fluid infusion system (and the individual operating components of the system) may not be described in detail here. Examples of infusion pumps used to administer insulin and other medications may be of the type described in, but not limited to, U.S. Pat. Nos. 6,485,465; 6,554,798; 6,558,351; 6,752,787; 6,932,584; and 7,621,893; which are herein incorporated by reference.

In accordance with certain exemplary embodiments described herein, a fluid infusion system utilizes a combined infusion-sensor unit that functions to: (1) deliver a medication fluid to the body of a patient; and (2) sense or detect a measurable analyte or physiological characteristic of the patient. The combined infusion-sensor unit may be configured as an infusion set component that is compatible with a tubing component that provides the medication fluid from a fluid infusion device to the infusion set component. The infusion set component may also be compatible with a sensor transmitter component that transmits sensor data to a device within the fluid infusion system, e.g., the fluid infusion device or a monitor device.

The infusion set component is designed to accommodate a fluid channel module, which is manufactured as a physically distinct and separate component having a self-contained fluid path defined therein. The fluid channel module is installed into a base component to form the infusion set component. In certain embodiments, the base component includes a universal interface feature that receives and secures the fluid channel module. The interface feature is "universal" in that it is shaped, sized, and otherwise configured for compatibility with a plurality of different fluid channel module types. Thus, the infusion set component can be offered in different configurations in a cost efficient manner by using the same base component and installing the desired fluid channel module type. For example, one fluid channel module type could employ a soft cannula for the fluid delivery conduit, and another fluid channel module type could employ a stiff metal needle for the fluid delivery conduit. As another example, fluid channel modules having different needle dimensions (e.g., lengths) could be offered.

As mentioned above, the fluid channel module defines the fluid flow path for the infusion set component. Thus, the fluid channel module can be tested by itself to check the integrity of the fluid flow path. If the integrity of the flow path does not satisfy the required performance specifications, then the fluid channel module can be scrapped without having to sacrifice the entire infusion set component. Consequently, the use of a physically distinct and separate fluid channel module can reduce manufacturing cost.

Referring now to the drawings, FIG. 1 is a schematic plan view of an exemplary embodiment of a fluid infusion system 100. The system 100 includes three main components: a fluid infusion device 102 (e.g., an insulin pump); an infusion set component 104; and a tubing connector component 106. FIG. 1 shows the system 100 in its assembled state—the tubing connector component 106 physically and fluidly couples the fluid infusion device 102 to the infusion set component 104. This particular embodiment of the tubing connector component 106 includes, without limitation: a tube 108; a reservoir connector 110 at one end of the tube 108; and a fluid tubing connector 112 at the other end of the tube 108. The reservoir connector 110 can be physically coupled to the fluid infusion device 102 to establish a fluid connection with a fluid reservoir 114, and the fluid tubing connector 112 can be physically coupled to the infusion set component 104 to establish a fluid connection with the infusion set component 104.

Although not always required, the exemplary embodiment of the infusion set component 104 is implemented as a combined infusion-sensor unit having a fluid infusion conduit for delivery of fluid from the fluid infusion device 102, and having an analyte sensor to sense or detect an analyte or physiological characteristic of the patient (such as blood glucose). In certain embodiments, the infusion set component 104 cooperates with a wireless sensor transmitter 116 such that data indicative of the measured analyte levels can be wirelessly transmitted to a compatible device, such as the fluid infusion device 102, a monitor device (not shown), a computing device (not shown), or the like.

The fluid infusion device 102 is designed to be carried or worn by the patient, and the tubing connector component 106 terminates at the infusion set component 104 such that the fluid infusion device 102 can deliver fluid to the body of the patient via the tube 108. The fluid infusion device 102 may leverage a number of conventional features, components, elements, and characteristics of existing fluid infusion devices. For example, the fluid infusion device 102 may incorporate some of the features, components, elements, and/or characteristics described in U.S. Pat. Nos. 6,485,465 and 7,621,893, the relevant content of which is incorporated by reference herein.

The fluid infusion device 102 accommodates the fluid reservoir 114 for the fluid that is delivered to the user. The tube 108 represents the fluid flow path that couples the fluid reservoir 114 to the infusion set component 104. When installed as depicted in FIG. 1, the tube 108 extends from the fluid infusion device 102 to the infusion set component 104, which in turn provides a fluid pathway to the body of the patient via a subcutaneous conduit. For the illustrated embodiment, the reservoir connector 110 is realized as a removable cap or fitting that is suitably sized and configured to accommodate replacement of fluid reservoirs (which are typically disposable) as needed. In this regard, the reservoir connector 110 is designed to accommodate the fluid path from the fluid reservoir 114 to the tube 108.

Figure 2:
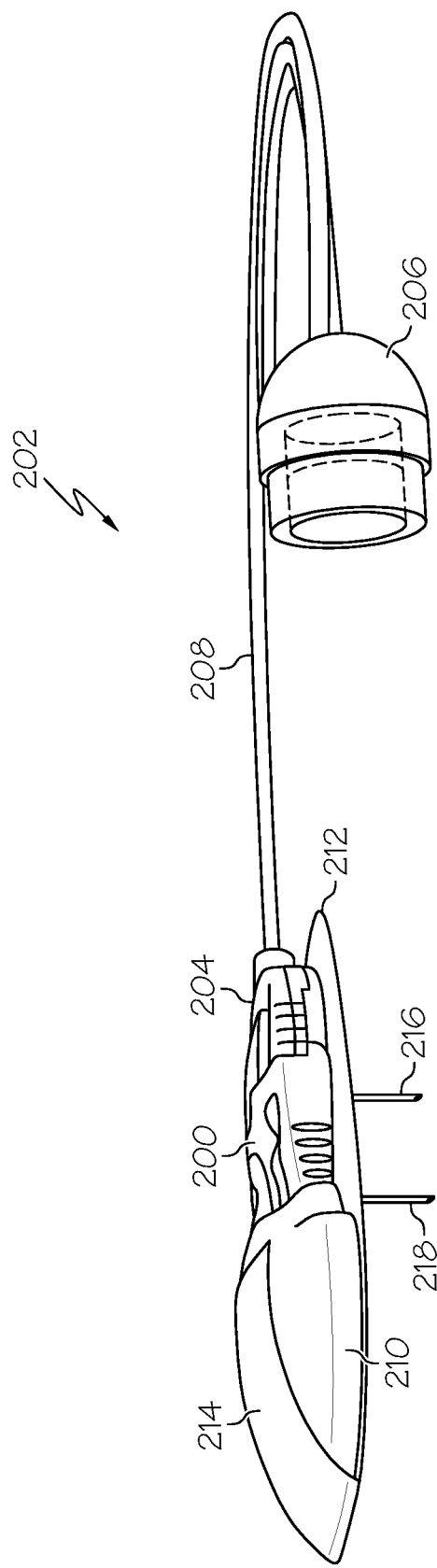
FIG. 2 is a perspective view of an exemplary embodiment of an infusion set component coupled to a tubing connector component.

FIG. 2 is a perspective view of an exemplary embodiment of an infusion set component 200 coupled to a tubing connector component 202. As mentioned above for the system 100, the tubing connector component 202 includes a fluid tubing connector 204, a reservoir connector 206, and a tube 208 coupled between the fluid tubing connector 204 and the reservoir connector 206. FIG. 2 also shows a wireless sensor transmitter 210 coupled to the infusion set component 200, and an adhesive layer 212 that serves to affix the infusion set component 200 and the wireless sensor transmitter 210 to the skin of the user. The adhesive layer 212 includes a flap 214 that folds over and onto the wireless sensor transmitter 210 to help retain the wireless sensor transmitter 210 in place.

FIG. 2 depicts the infusion set component 200, the wireless sensor transmitter 210, and the tubing connector component 202 as worn by the patient. Thus, the tubing connector component 202 is physically and fluidly coupled to the infusion set component 200. As described in more detail below, the infusion set component 200 includes a conduit 216 in fluid communication with the tube 208. When in use, the conduit 216 is located subcutaneously to deliver the fluid from the fluid infusion device (not shown in FIG. 2) to the patient via the tubing connector component 202. The illustrated embodiment of the infusion set component 200 also includes a sensor 218 to facilitate sensing of an analyte of the patient. For example, the sensor 218 could be an enzyme-based electrochemical biosensor of the type normally used to detect blood glucose levels. In accordance with established sensor technology, the sensor 218 cooperates with the wireless sensor transmitter 210 to provide sensor data that corresponds to real-time measurements of the monitored analyte. It should be appreciated that the infusion set component 200 need not be realized as a combined infusion-sensor unit, and that alternative embodiments of the infusion set component 200 may be realized without the sensor 218.

Figure 3:
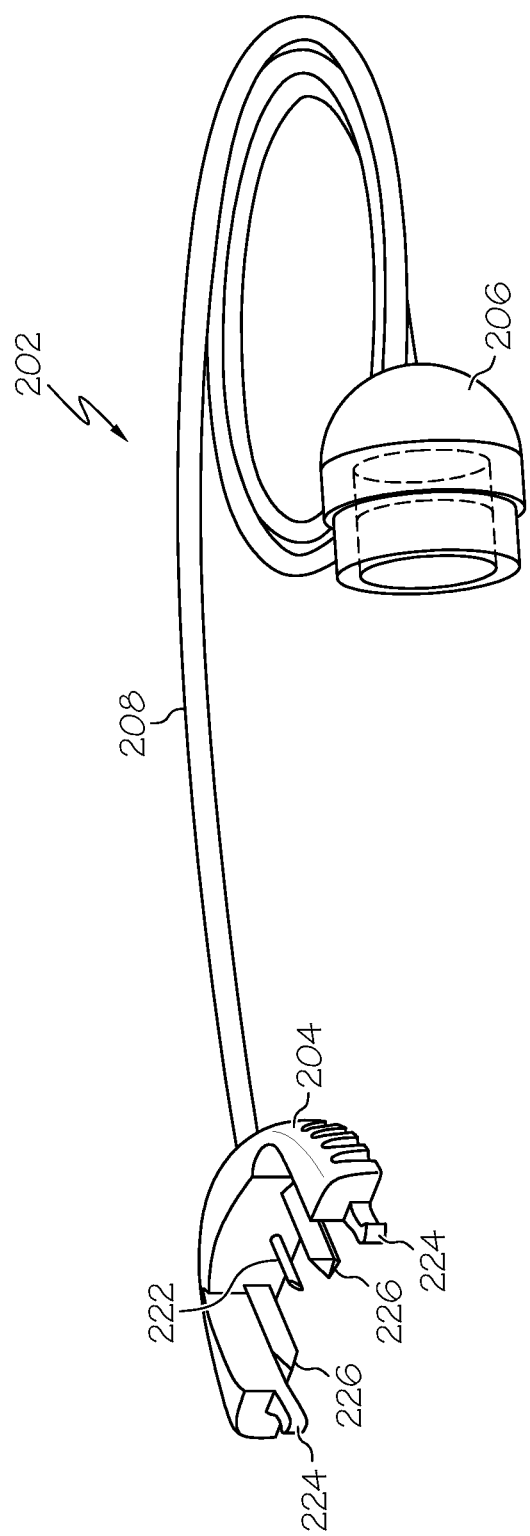
FIG. 3 is a perspective view of the tubing connector component.

FIG. 3 is a perspective view of the tubing connector component 202 by itself. The fluid tubing connector 204 includes a hollow connector needle 222 that represents one end of the flow path defined by the tubing connector component 202. In other words, the connector needle 222 is fluidly coupled to the tube 208. The fluid tubing connector 204 also includes certain features and structure that are configured to mate with corresponding features and structure found on the infusion set component 200. In this regard, the illustrated embodiment of the fluid tubing connector 204 includes snap arms 224 and guide arms 226 that engage corresponding features of the infusion set component 200 (see FIG. 9). The snap arms 224 deflect when the fluid tubing connector 204 is forced to engage the infusion set component 200 and eventually snap in place to lock the fluid tubing connector 204 to the infusion set component 200. The fluid tubing connector 204 can be removed from the infusion set component 200 by squeezing inwardly on the fluid tubing connector 204 such that the snap arms deflect and release the infusion set component 200. The guide arms 226 mate with corresponding slots formed in the infusion set component 200. The guide arms 226 ensure that the connector needle 222 is properly oriented during installation.

Figure 4:
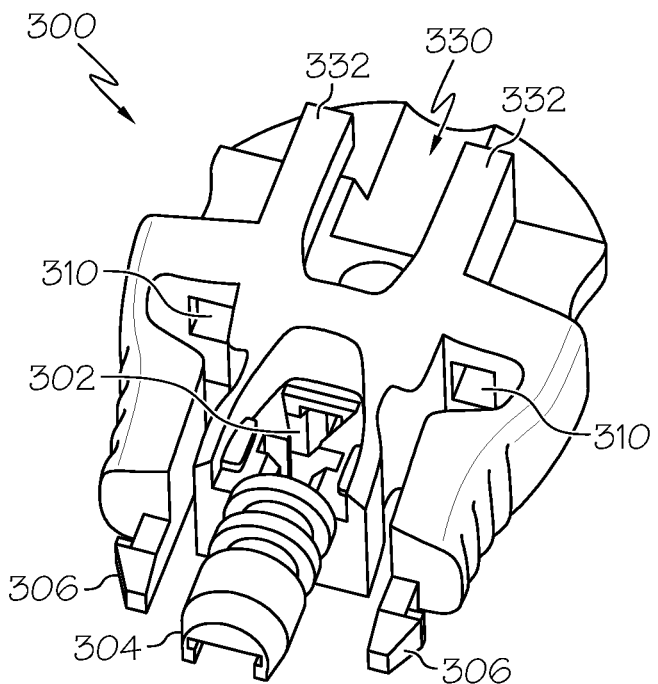
FIG. 4 is a perspective top view of an exemplary embodiment of a base suitable for use with the infusion set component shown in FIG. 2.
Figure 5:
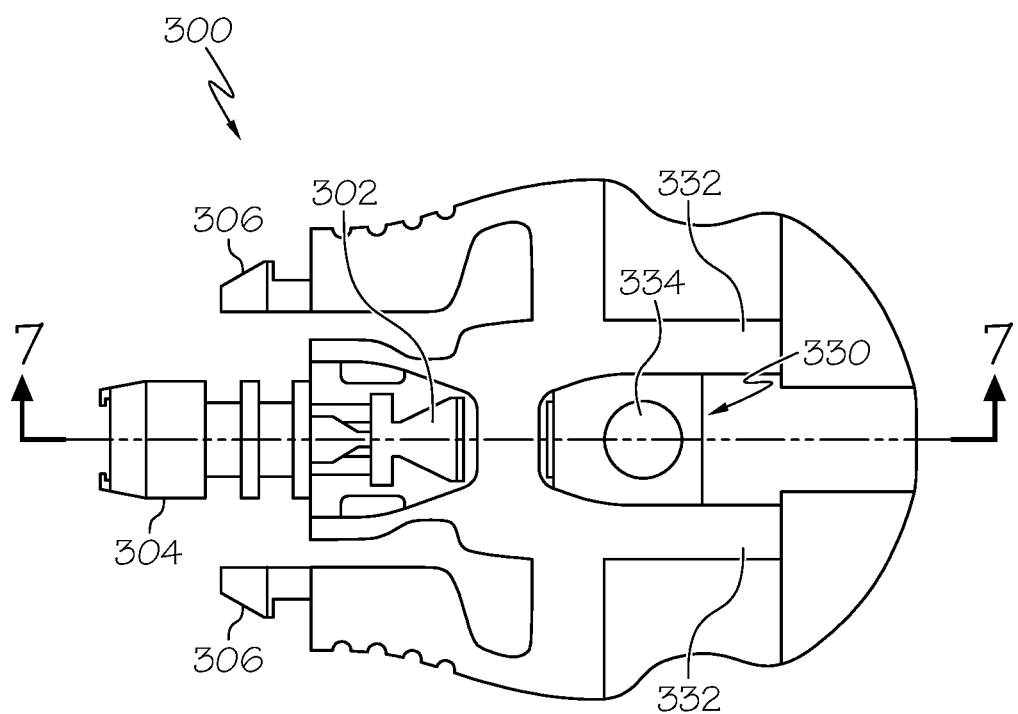
FIG. 5 is a top view of the base shown in FIG. 4.
Figure 6:
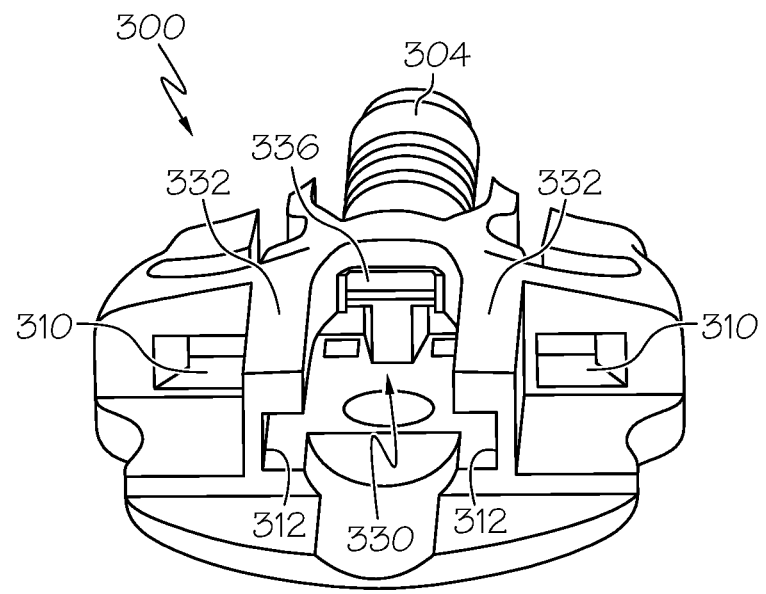
FIG. 6 is a perspective end view of the base shown in FIG. 4.
Figure 7:
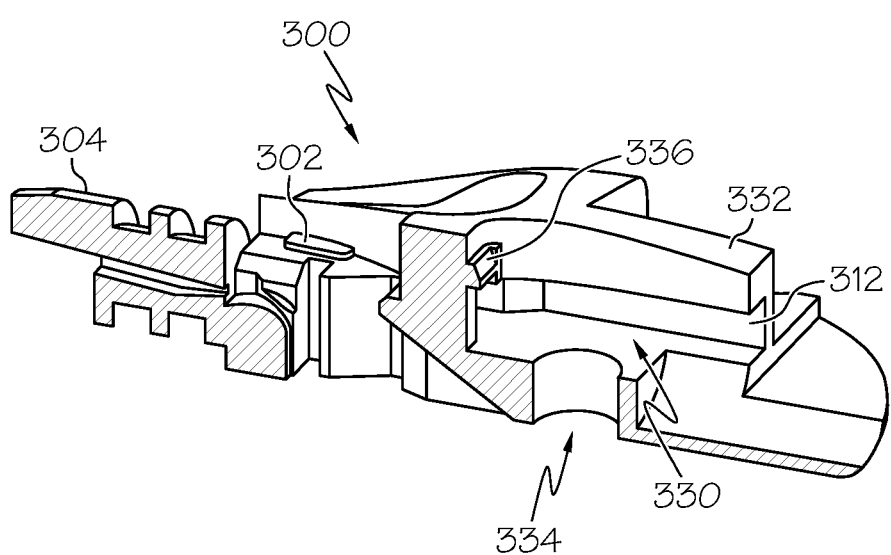
FIG. 7 is a perspective cross-sectional view of the base, corresponding to a section taken at line 7-7 in FIG. 5.

In certain embodiments, the infusion set component 200 includes a base and a fluid channel module coupled to the base. The fluid channel module can be manufactured as a separate component that becomes inseparable from the base after assembly. Notably, the fluid channel module is designed to completely define the fluid flow path for the infusion set component 200. FIGS. 4-7 show an exemplary embodiment of a base body section 300 that is suitable for use with the infusion set component 200. FIG. 4 is a perspective top view of the base body section 300, FIG. 5 is a top view of the base body section 300, FIG. 6 is a perspective end view of the base body section 300, and FIG. 7 is a perspective cross-sectional view of the base body section 300 (corresponding to a section taken at line 7-7 in FIG. 5). The base body section 300 may be realized as a unitary, one-piece component fabricated from a suitable material such as plastic, nylon, or the like. In certain embodiments, the base body section 300 is a single-piece molded component.

The base body section 300 includes features that accommodate the sensor 218 and the wireless sensor transmitter 210 (see FIG. 2). For example, the base body section 300 includes a sensor cap cavity 302 or other sensor interface formed therein. The sensor cap cavity 302 is shaped, sized, and otherwise configured to receive, accommodate, and maintain a sensor cap (not shown in FIGS. 4-7, but partially visible in FIG. 2) that facilitates insertion of the sensor 218 into the body of the patient. Thus, when the sensor cap is installed in the sensor cap cavity 302, the sensor 218 is coupled to the base body section 300. The base body section 300 also includes a neck region 304 and snap arms 306 that mate with the wireless sensor transmitter 210. The neck region 304 can be used to establish a physical and electrical connection between the wireless sensor transmitter 210 and the sensor 218. The snap arms 306 allow the base body section 300 to be removably coupled to the wireless sensor transmitter 210.

Figure 9:
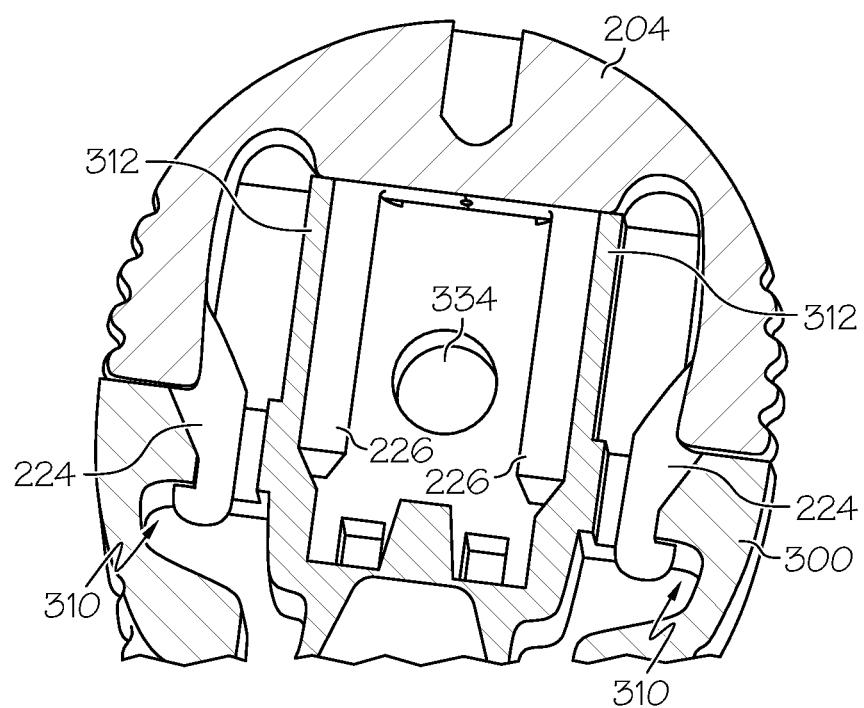
FIG. 9 is a cross-sectional view of the assembly shown in FIG. 8, as viewed along line 9-9.

The base body section 300 also includes one or more attachment features that accommodate removable coupling with the fluid tubing connector 204 (see FIG. 3). For example, the base body section 300 may include snap arm catches 310 and guide arm slots 312 that correspond to the snap arms 224 and the guide arms 226, respectively. The snap arm catches 310 are shown in FIGS. 4, 6, 7, and 9; the guide arm slots 312 are shown in FIGS. 6, 7, and 9. In certain embodiments, the snap arm catches 310 and/or the guide arm slots 312 are integrally formed with the base body section 300.

Figure 8:
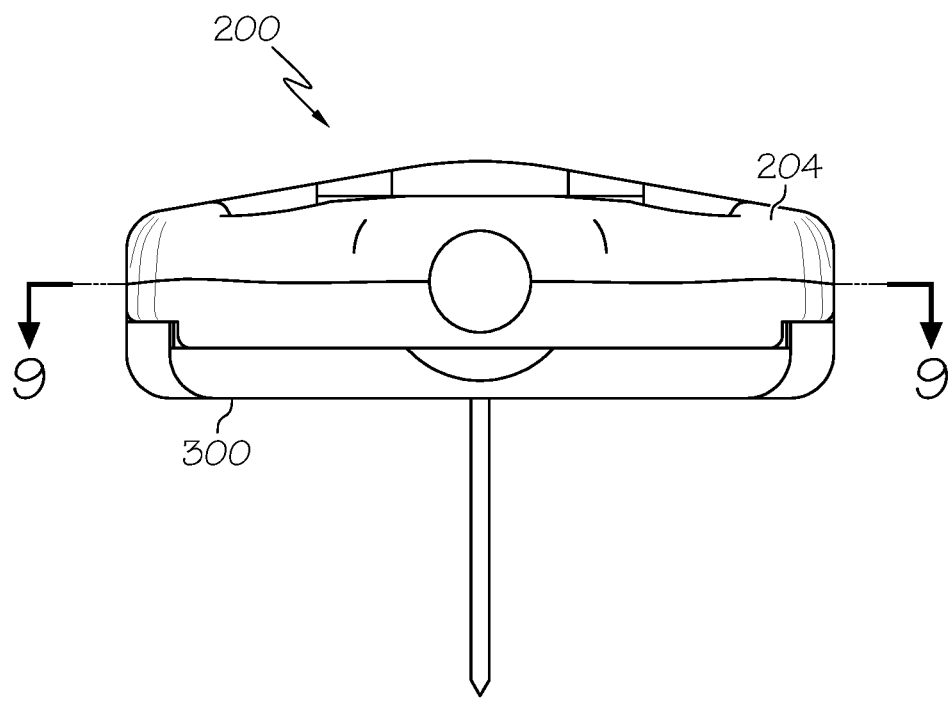
FIG. 8 is an end view of the infusion set component shown in FIG. 2, together with a fluid tubing connector.

FIG. 8 is an end view of the infusion set component 200, along with the fluid tubing connector 204, and FIG. 9 is a cross-sectional view of the assembly shown in FIG. 8, as viewed along the line 9-9. FIG. 9 illustrates the manner in which the snap arms 224 of the fluid tubing connector 204 engage and couple to the snap arm catches 310 to secure the fluid tubing connector 204 to the base body section 300. FIG. 9 also illustrates the manner in which the guide arms 226 of the fluid tubing connector 204 engage and mate with the guide arm slots 312 of the base body section 300. For clarity and ease of illustration, FIG. 9 does not include some of the structure and elements that would ordinarily be present in an actual cross-section (e.g., the connector needle 222, which is shown in FIG. 3).

The base body section 300 also includes a fluid channel module interface 330 formed therein. In certain embodiments, the fluid channel module interface 330 is integrally formed in the base body section 300 (e.g., by machining, molding, or the like). As shown in FIGS. 4-7, the fluid channel module interface 330 resembles a cavity or a receptacle in the base body section 300. The fluid channel module interface 330 is suitably configured to receive and maintain the fluid channel module for the infusion set component. The fluid channel module interface 330 includes universal coupling features that mate with corresponding universal coupling features of a fluid channel module (described in more detail below). These coupling features are "universal" in that the fluid channel module interface 330 can universally accommodate a plurality of different fluid channel module types having compatible coupling/mounting features. For example, one fluid channel module may include a rigid metal needle, another fluid channel module may include a soft cannula, etc. Moreover, such universal coupling features could be incorporated into a base body section (not shown) for a fluid injection port that receives a corresponding fluid channel module, which in turn facilitates delivery of fluid via a user-inserted syringe needle. An exemplary embodiment of a fluid injection port implementation is described in more detail below with reference to FIG. 24. Regardless of the specific configuration and characteristics of the chosen fluid channel module, the universal coupling features can be standardized to allow a user or a manufacturer to select any one of a plurality of different fluid channel modules for use with the infusion set component.

For the illustrated embodiment of the base body section 300, the universal coupling features include, without limitation: two rails 332; a hole 334; and a lock tab 336 or other locking mechanism. These coupling features may be dimensioned with somewhat tight tolerances such that no adhesive or glue is needed to maintain the module in place. That said, adhesive, glue, bonding, or welding techniques could be utilized to reinforce this coupling. Notably, the distance between the two rails 332, the height of the two rails 332, the location, shape, and size of the hole 334, the location, shape, and size of the lock tab 336, the fore-aft dimensions of the two rails 332, and possibly other dimensions and characteristics of the fluid channel module interface 330 are defined for standardization with the different available fluid channel modules. Thus, although the internal construction and/or the particular specifications of the fluid conduits may vary from one fluid channel module to another, certain dimensions and features of all fluid channel modules will be compatible with the corresponding dimensions and features of the base body section 300. The function of these universal coupling features are described in more detail below.

Figure 10:
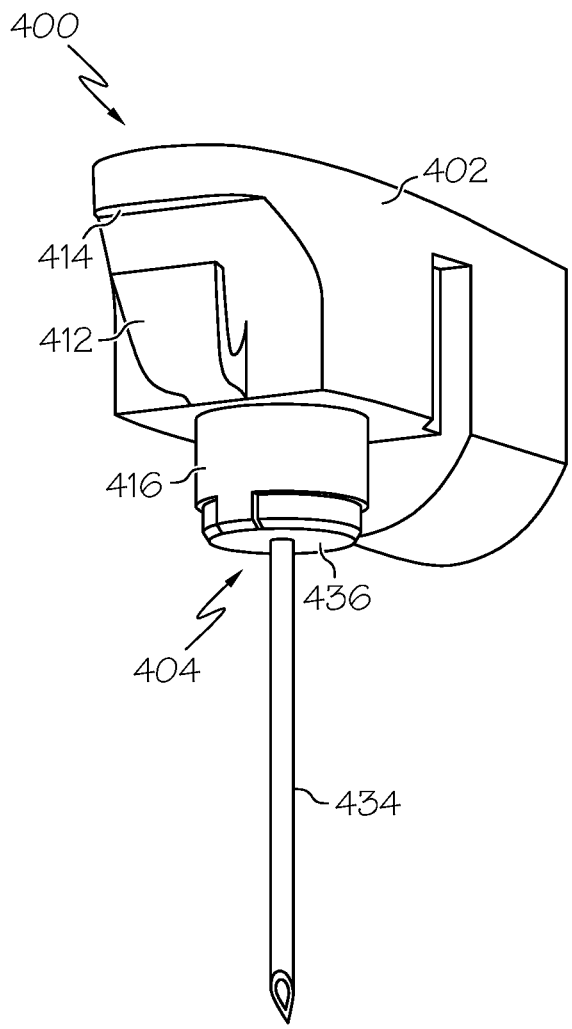
FIG. 10 is a perspective view of an exemplary embodiment of a fluid channel module suitable for use with the infusion set component shown in FIG. 2.
Figure 11:
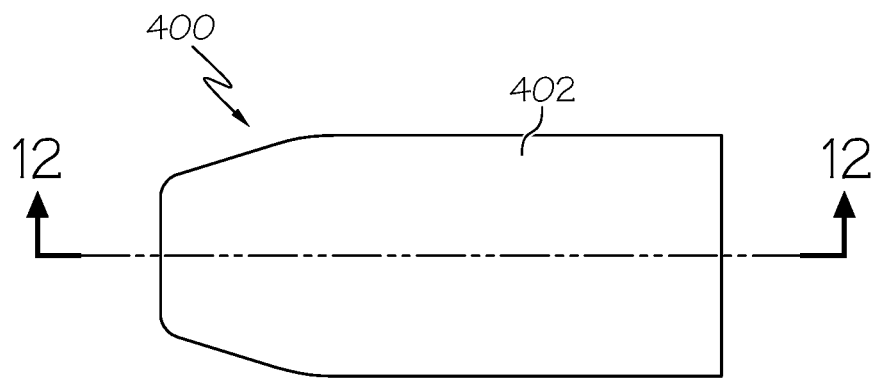
FIG. 11 is a top view of the fluid channel module shown in FIG. 10.
Figure 12:
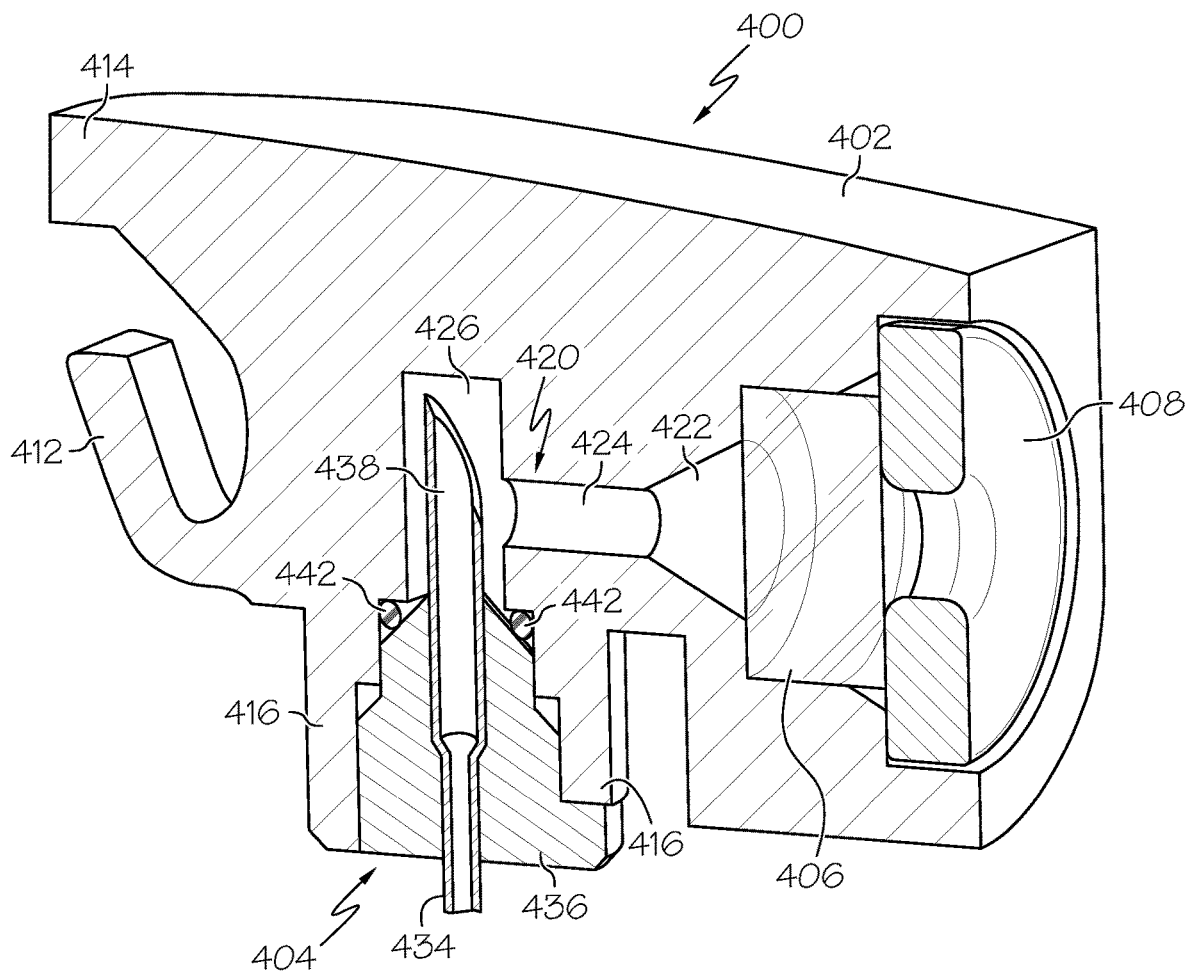
FIG. 12 is a perspective cross-sectional view of a portion of the fluid channel module, corresponding to a section taken at line 12-12 in FIG. 11.

FIGS. 10-12 depict an exemplary embodiment of a fluid channel module 400 suitable for use with the infusion set component 200. FIG. 10 is a perspective view of the fluid channel module 400, FIG. 11 is a top view of the fluid channel module 400, and FIG. 12 is a perspective cross-sectional view of the upper section of the fluid channel module 400, corresponding to a section taken at line 12-12 in FIG. 11. This particular embodiment of the fluid channel module 400 includes, without limitation: a body section 402; a needle assembly 404 (shown by itself in FIG. 13); a septum 406; and a septum cap 408. Notably, the fluid channel module 400 represents one module type that is compatible with the universal coupling features of the base body section 300.

The body section 402 may be realized as a unitary, one-piece component fabricated from a suitable material such as plastic, nylon, or the like. In certain embodiments, the body section 402 is a single-piece molded component. The body section 402 includes one or more coupling features that are suitably configured to mate with and couple to the universal coupling features of the base body section 300. For example, the body section 402 may include or cooperate with a snap hook 412 that engages the lock tab 336 of the base body section 300 (see FIG. 14, which illustrates the manner in which the body section 402 engages and couples with the base body section 300). The body section 402 may also include a retaining lip 414 that rests against the upper portion of the lock tab 336 when the fluid channel module 400 is installed in the base body section 300 (see FIG. 14). Thus, the snap hook 412 deflects around the lock tab 336 when the fluid channel module 400 is urged into the fluid channel module interface 330. The snap hook 412 springs back into its nominal position (shown in FIG. 14) when the fluid channel module 400 is seated within the fluid channel module interface 330, which prevents the fluid channel module 400 from falling out of the base body section 300. In this regard, the combination of the snap hook 412 and the lock tab 336 may be considered to be one implementation of a universal locking mechanism for the infusion set component 200.

Figure 14:
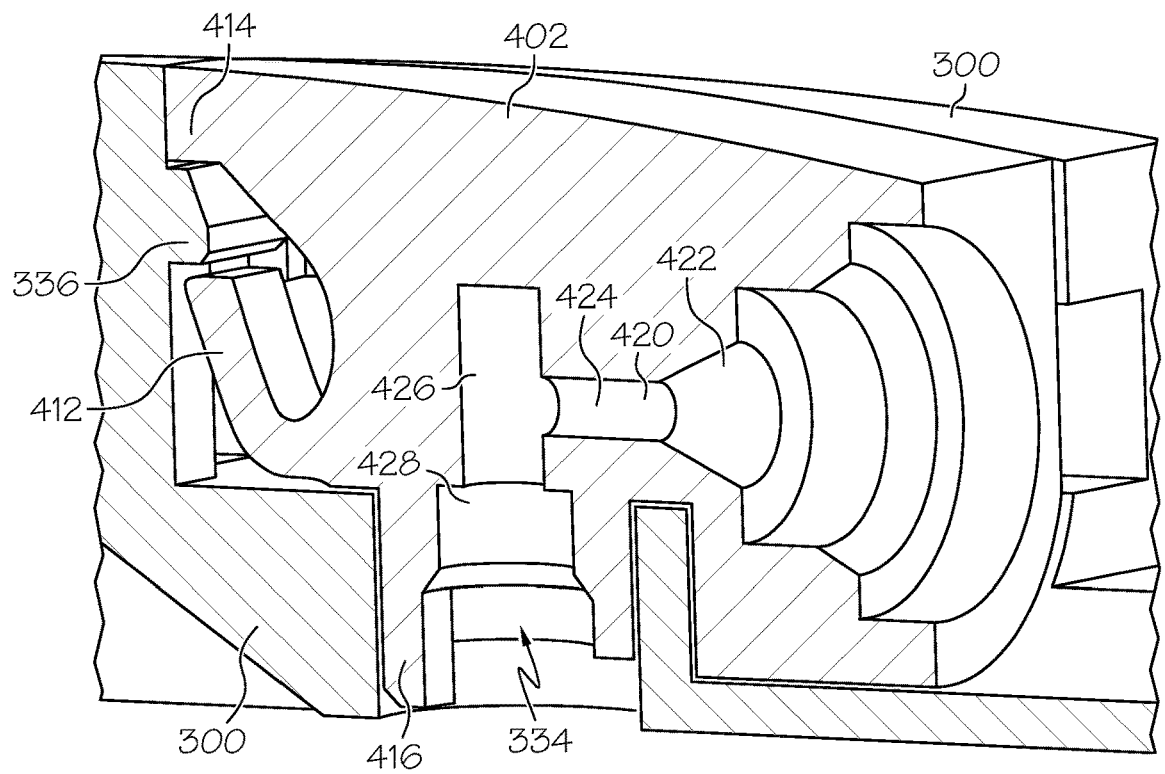
FIG. 14 is a perspective cross-sectional view that depicts a body section of the fluid channel module installed in a base of an infusion set component.
Figure 15:
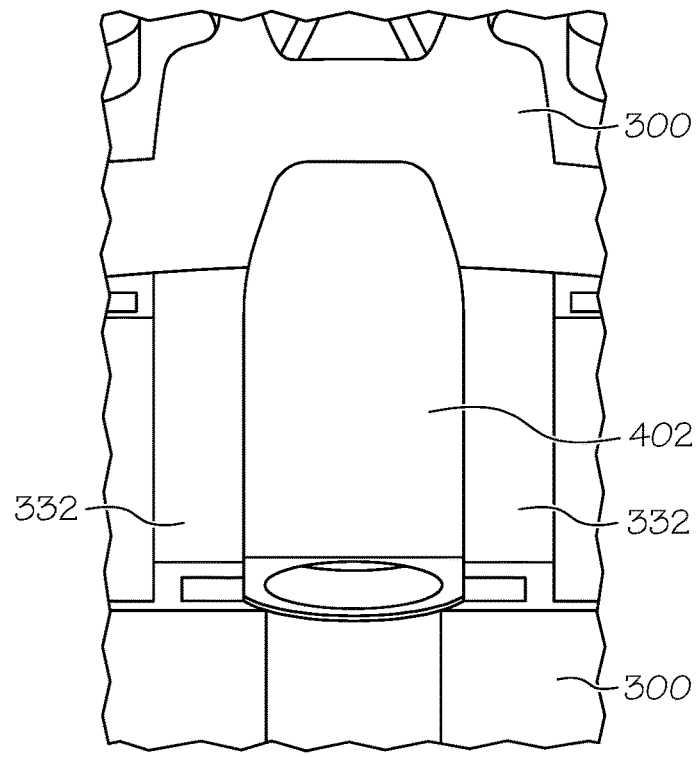
FIG. 15 is a perspective top view that depicts a body section of the fluid channel module installed in a base of an infusion set component.

The body section 402 may also include an outlet port 416 that extends to accommodate the needle assembly 404. For this particular embodiment, the outer surface of the port 416 is cylindrical in shape, although other shapes and contours could be utilized. Notably, the hole 334 formed within the base body section 300 is universally shaped and sized to mate with the port 416. Referring again to FIGS. 4-7, the hole is formed in the base body section 300 such that it communicates with the cavity that is used for the fluid channel module interface 330, and such that it leads to the bottom of the base body section 300. As shown in FIG. 14, the hole 334 is located and oriented such that the port 416 retains the body section 402 in position when the fluid channel module 400 is seated in the base body section 300. In practice, the hole 334 is shaped, sized, and located for universal compatibility with the ports of one or more additional fluid channel modules, as mentioned above.

Referring to FIG. 14, the fluid channel module 400 includes an interior fluid flow channel 420 formed and defined within the body section 402. The fluid flow channel 420 is arranged to receive the fluid from the fluid infusion device (more specifically, from the connector needle 222 of the fluid tubing connector 204), and provide the fluid for dispensing from the needle assembly 404. The illustrated embodiment of the fluid flow channel 420 includes an inlet 422, a first segment 424, a needle entry zone 426, and an outlet 428. During fluid delivery operations, the fluid enters the inlet 422, flows through the first segment 424 and into the needle entry zone 426, and flows through the needle of the needle assembly 404. As described in more detail below, the fluid channel module 400 may include one or more seals, septa, or other elements that prevent leakage such that the fluid pressure generated during fluid delivery operations urges the fluid out of the delivery needle.

Figure 13:
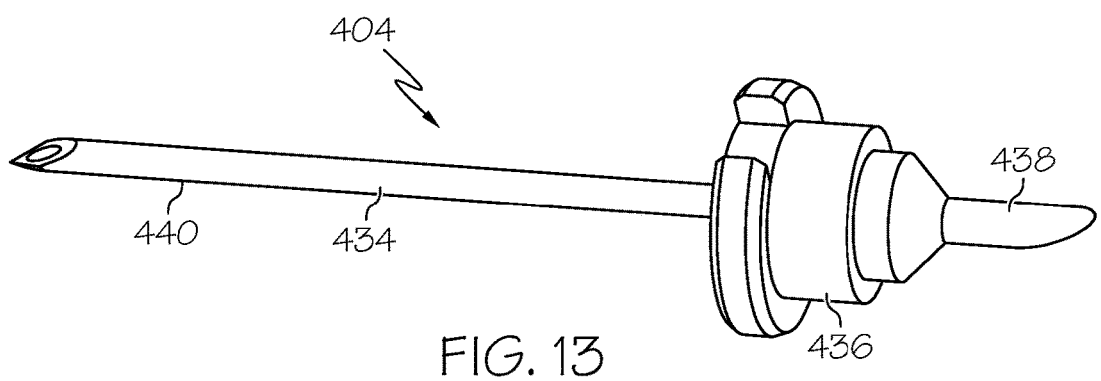
FIG. 13 is a perspective view of an exemplary embodiment of a needle assembly suitable for use with the fluid channel module shown in FIG. 10.

Referring back to FIGS. 10-13, the illustrated embodiment of the needle assembly 404 includes a rigid hollow needle 434 and a needle hub 436 coupled to the needle 434. As best shown in FIG. 13, the needle hub 436 is coupled around a section of the exterior surface of the needle 434. In certain embodiments, the needle hub 436 is coupled to the needle 434 at a position along the length of the needle 434 such that only a short segment of the needle 434 (corresponding to the inlet end 438) extends above the needle hub 436, and such that most of the needle 434 (corresponding to the outlet end 440) extends below the needle hub 436. The segment of the needle 434 below the needle hub 436 represents the subcutaneous segment. During manufacturing, the needle assembly 404 is secured to the body section 402. As shown in FIG. 10 and FIG. 12, the needle hub 436 is affixed to the body section 402 of the fluid channel module 400 such that the inlet end 438 resides in (or fluidly communicates with) the needle entry zone 426. In practice, the needle assembly 404 may be coupled to the body section 402 by way of a snap fit, tabs, or other mechanical means. Alternatively or additionally, the needle hub 436 can be ultrasonically welded, bonded, or otherwise attached to the port 416 to form a fluid tight seal between the needle hub 436 and the port 416. Consequently, the needle 434 is coupled to the body section 402 in a fixed position, which is desirable to facilitate insertion into the body of the patient using, for example, a suitably configured insertion mechanism or device. Although not always required, the fluid channel module 400 may also include a sealing element 442 (FIG. 12) to form an additional fluid seal between the needle hub 436 and the body section 402. For example, the sealing element 442 may be realized as an "O" ring positioned at an upper shoulder of the needle hub 436, as depicted in FIG. 12.

The needle 434 represents one suitable implementation of a fluid delivery conduit for the infusion set component 200. The inlet end 438 of the needle 434 is in fluid communication with the interior fluid flow channel 420, and the needle 434 cooperates with the interior fluid flow channel 420 to form a self-contained and defined fluid flow path to the patient. When the fluid channel module 400 is secured in the base body section 300, the needle 434 passes through and extends from the hole 334. Thus, the needle 434 protrudes from the bottom of the infusion set component 200, as shown in FIG. 2.

Referring again to FIG. 12, the septum 406 is located and held in place in the body section 402 by the septum cap 408. For this particular embodiment, the septum 406 is realized as a small disc-shaped or cylindrical plug. The septum 406 may be formed from a soft, resilient, and pliable material that has certain self-sealing or self-restoring properties. For example, the septum 406 may be formed from a silicone rubber material in certain embodiments. Depending upon the embodiment, the septum 406 may be provided in a solid and continuous form, or it may be provided with a slit, a cut, or an equivalent feature that makes it easier to pierce while still maintaining at least a nominal seal. The septum 406 has a nominal non-pierced state (depicted in FIG. 12) where the septum 406 seals the inlet 422 of the interior fluid flow channel 420 when the fluid tubing connector 204 is removed from the infusion set component 200 and, consequently, the connector needle 222 is removed from the septum 406. However, when the fluid tubing connector 204 is coupled to the infusion set component 200, the septum 406 is pierced by the connector needle 222 such that the connector needle 222 is fluidly coupled to the interior fluid flow channel 420.

Figure 16:
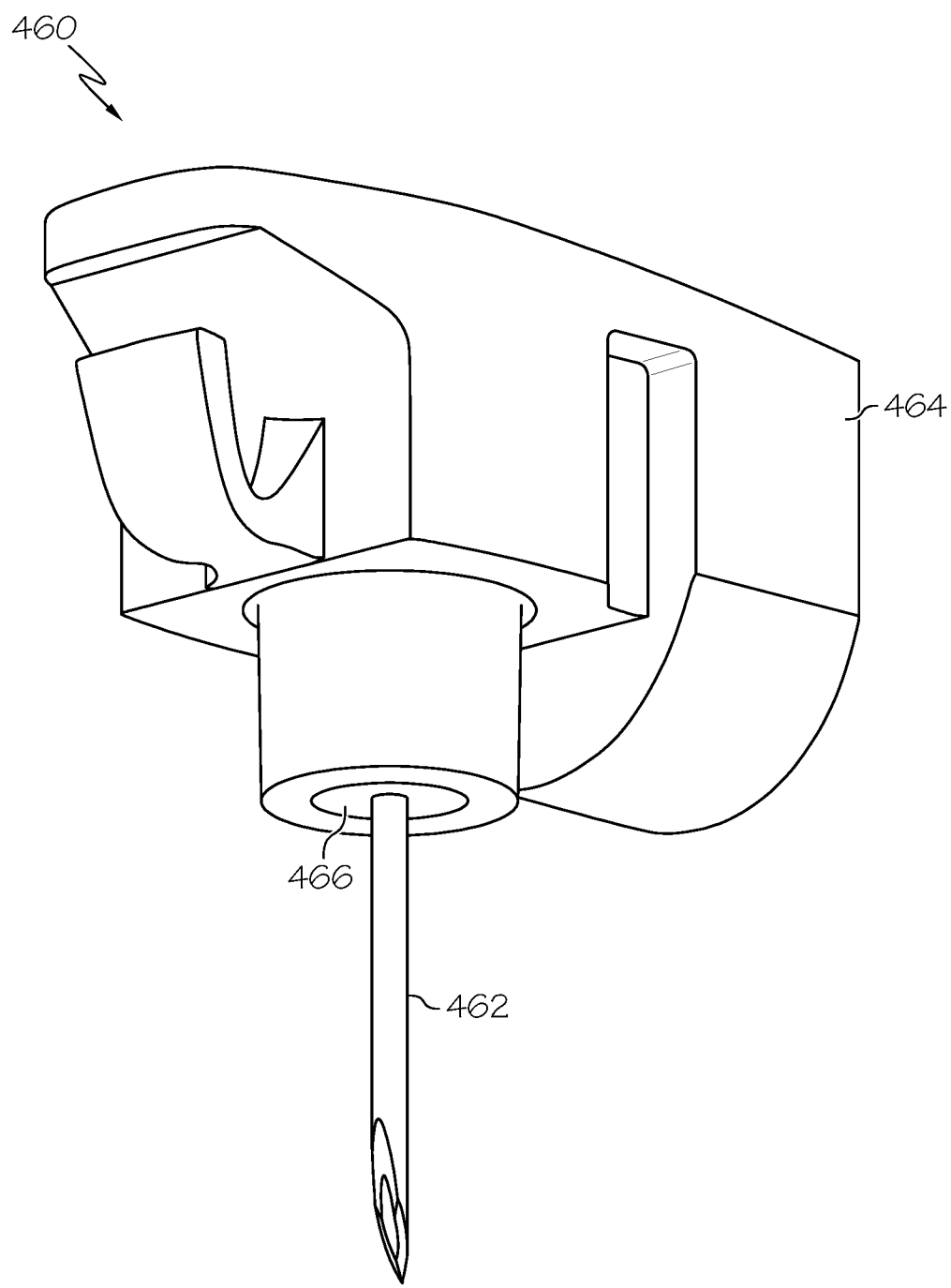
FIG. 16 is a perspective bottom view of another exemplary embodiment of a fluid channel module.
Figure 17:
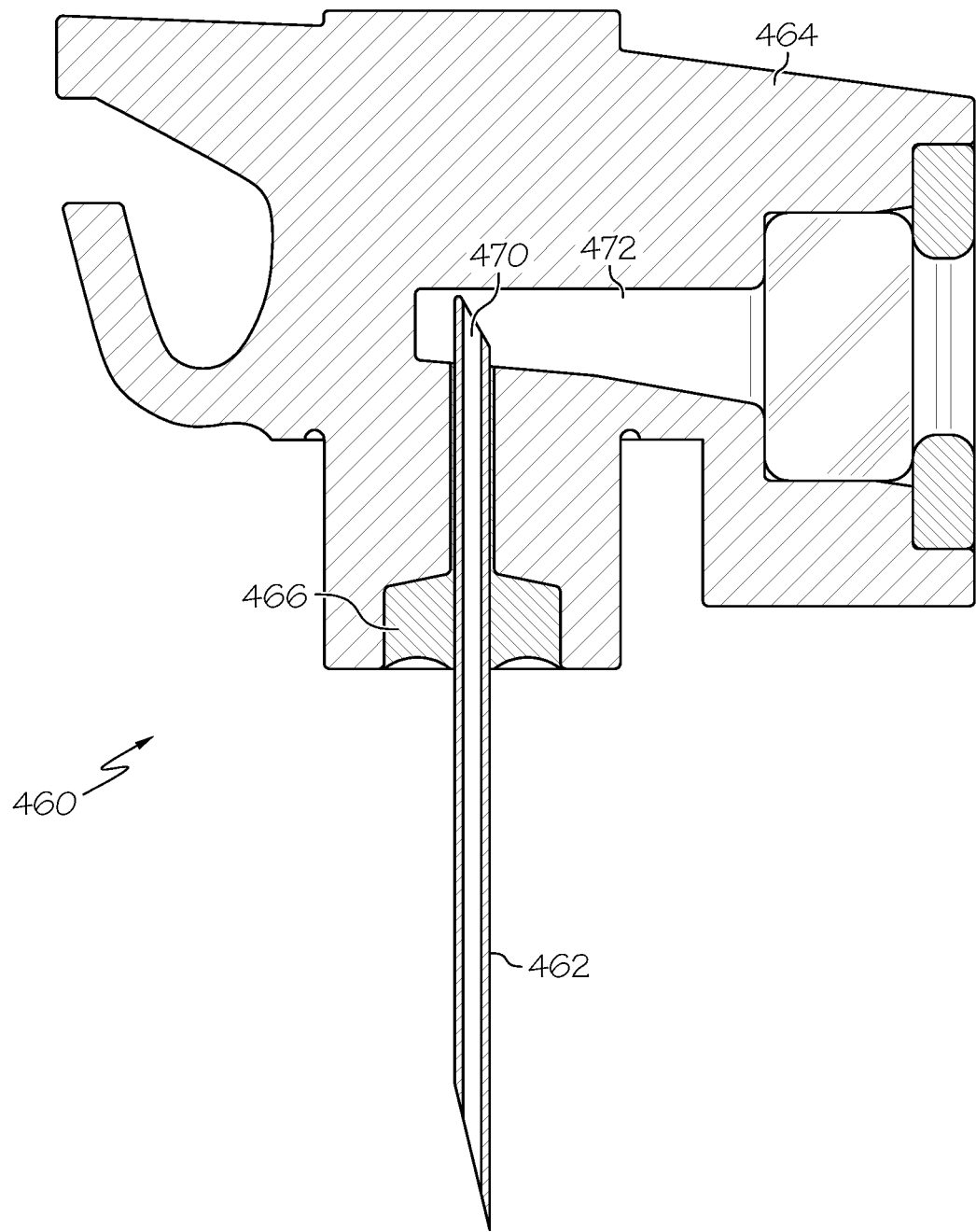
FIG. 17 is a cross-sectional view of the fluid channel module shown in FIG. 16.
Figure 18:
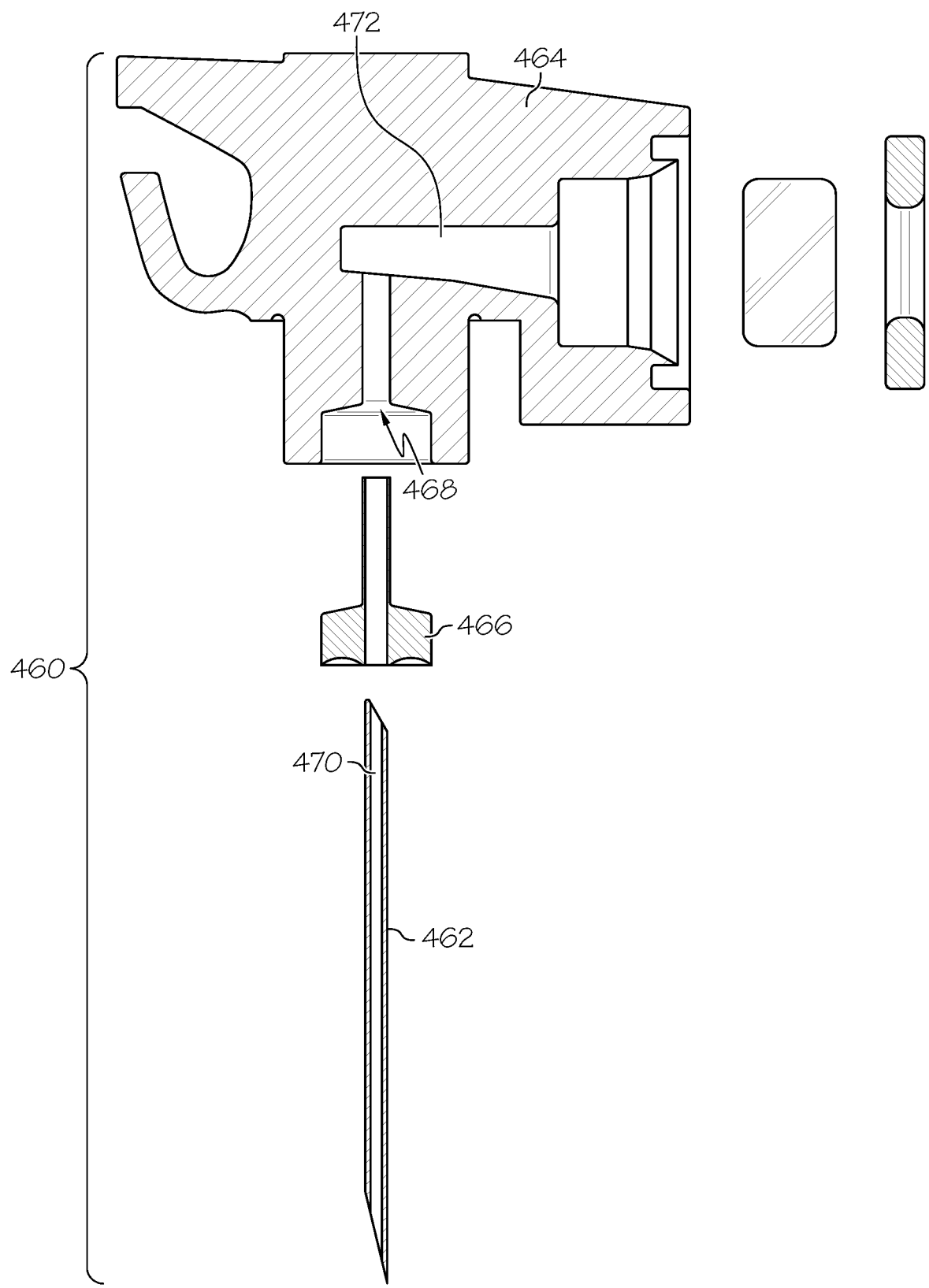
FIG. 18 is an exploded cross-sectional view of the fluid channel module shown in FIG. 16.

FIG. 16 is a perspective bottom view of another exemplary embodiment of a fluid channel module 460, FIG. 17 is a cross-sectional view of the fluid channel module 460, and FIG. 18 is an exploded cross-sectional view of the fluid channel module 460. The fluid channel module 460 shares some features and elements with the fluid channel module 400. For the sake of brevity, common features, characteristics, and functional aspects will not be redundantly described here in the context of the fluid channel module 460.

The fluid channel module 460 utilizes a different needle configuration than the fluid channel module 400. More specifically, the fluid channel module 460 includes a rigid needle 462 that is glued into the body section 464 (in contrast, the fluid channel module 400 employs the needle assembly 404, which may be attached via a snap fit, a press fit, or any suitable physical interconnection). For ease of understanding, FIGS. 16-18 show some adhesive 466 (alternatively, glue, a bonding agent, a welding agent, or any suitable composition) that facilitates attachment of the needle 462 to the body section 464. As best shown in FIG. 17, the adhesive 466 is located in a cavity 468 defined within the body section 464 to secure and maintain the needle 462 such that the upper end 470 of the needle 462 resides within a fluid flow channel 472 of the fluid channel module 460. During assembly of the fluid channel module 460, the needle 462 can be inserted into the cavity 468 and held in place using, for example, a jig or other tool. The uncured adhesive 466 can then be deposited within the cavity 468 to surround the needle 462, as shown in FIG. 16. Once set, the adhesive 466 affixes the needle 462 to the body section 464 in a fluid-tight manner that ideally prevents fluid leakage. This needle arrangement may be easier and less expensive to manufacture than the counterpart arrangement described above for the fluid channel module 400.

As mentioned previously, the fluid channel modules 400, 460 are compatible with the universal coupling and attachment features of the base body section 300. Thus, the fluid channel module interface 330 of the base body section 300 can receive and maintain the fluid channel modules 400, 460 to form a needle-based combined infusion-sensor unit if so desired to suit the needs of the patient. Alternatively, a different type of fluid channel module could be installed if needed. In this regard, FIGS. 19-22 relate to an alternative embodiment of a fluid channel module 500 that employs a pliable cannula instead of a rigid hollow needle. The fluid channel module 500 shares some features and elements with the fluid channel module 400. For the sake of brevity, common features, characteristics, and functional aspects will not be redundantly described here in the context of the fluid channel module 500.

Figure 19:
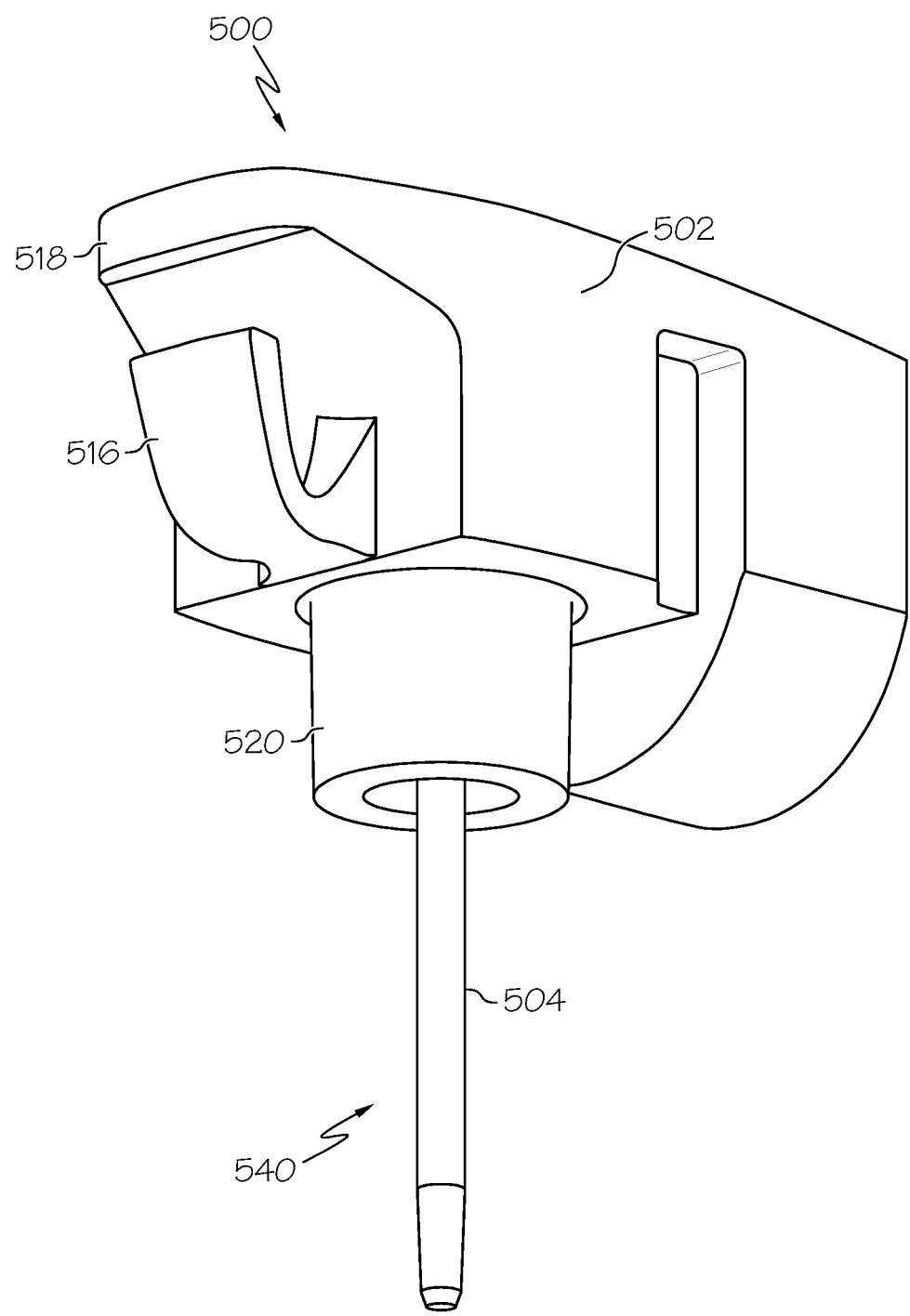
FIG. 19 is a perspective view of an another exemplary embodiment of a fluid channel module suitable for use with the infusion set component shown in FIG. 2.
Figure 20:
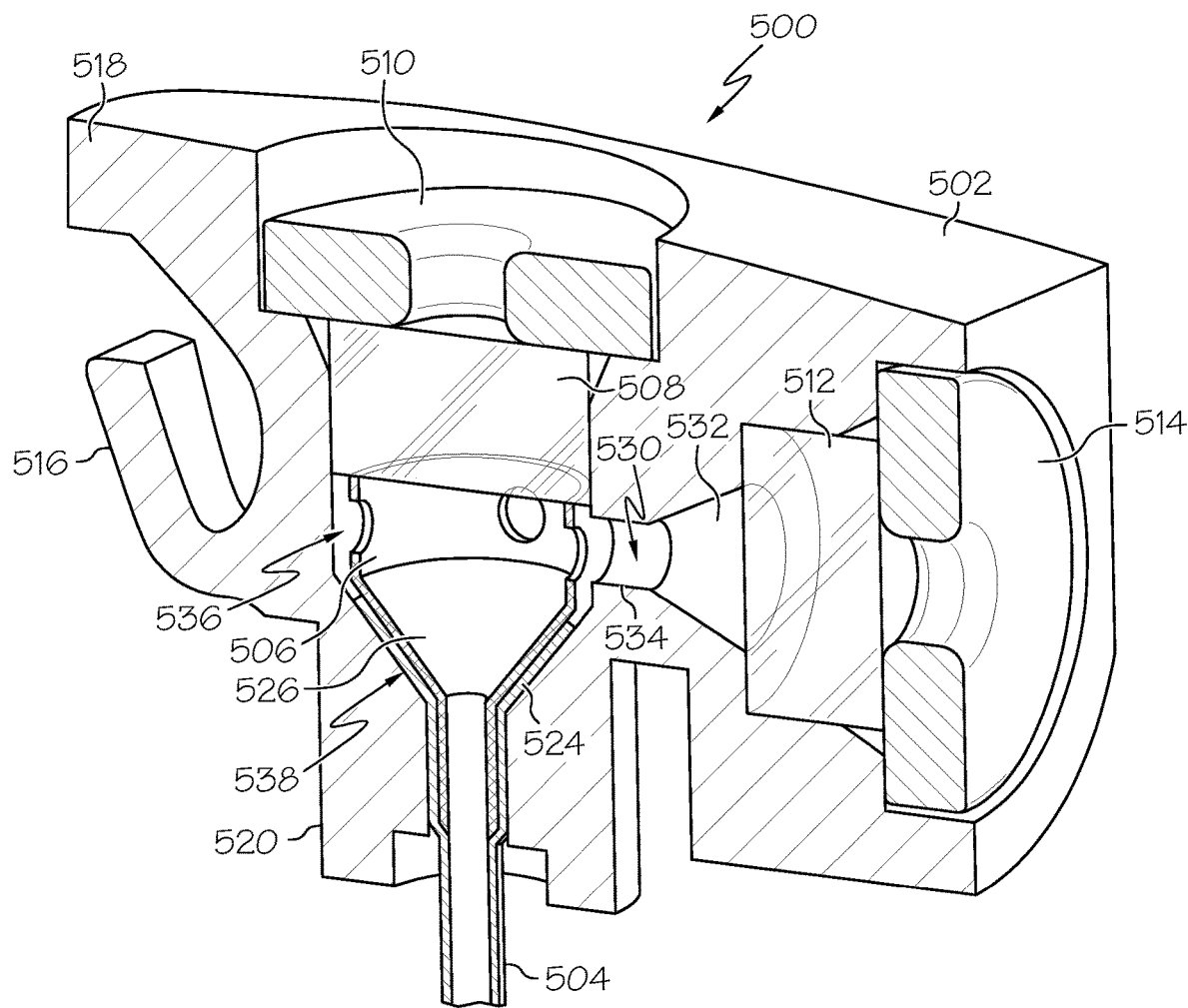
FIG. 20 is a perspective cross-sectional view of the fluid channel module shown in FIG. 19.
Figure 21:
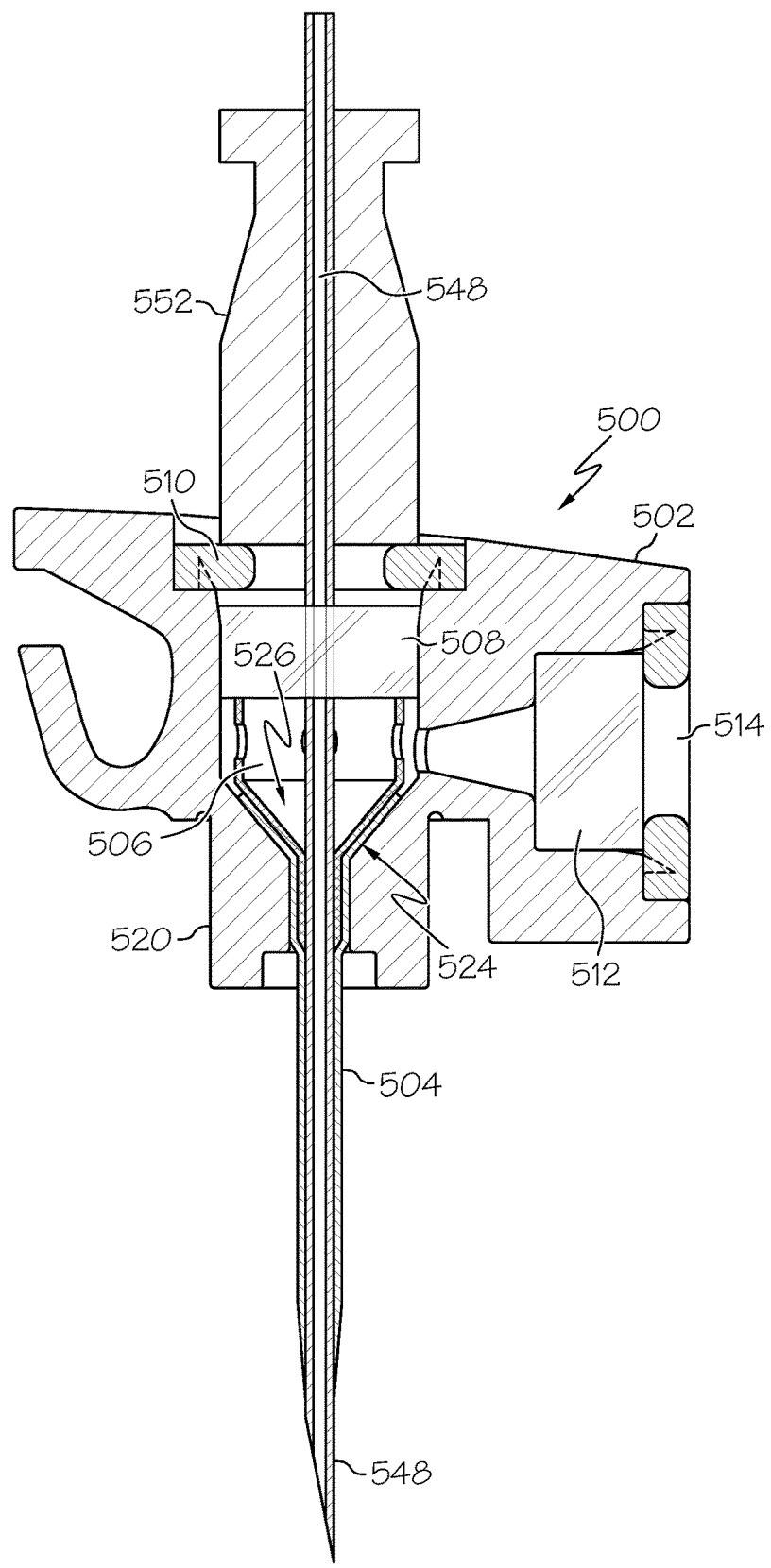
FIG. 21 is a cross-sectional view of the fluid channel module shown in FIG. 19, together with a needle introducer component.
Figure 22:
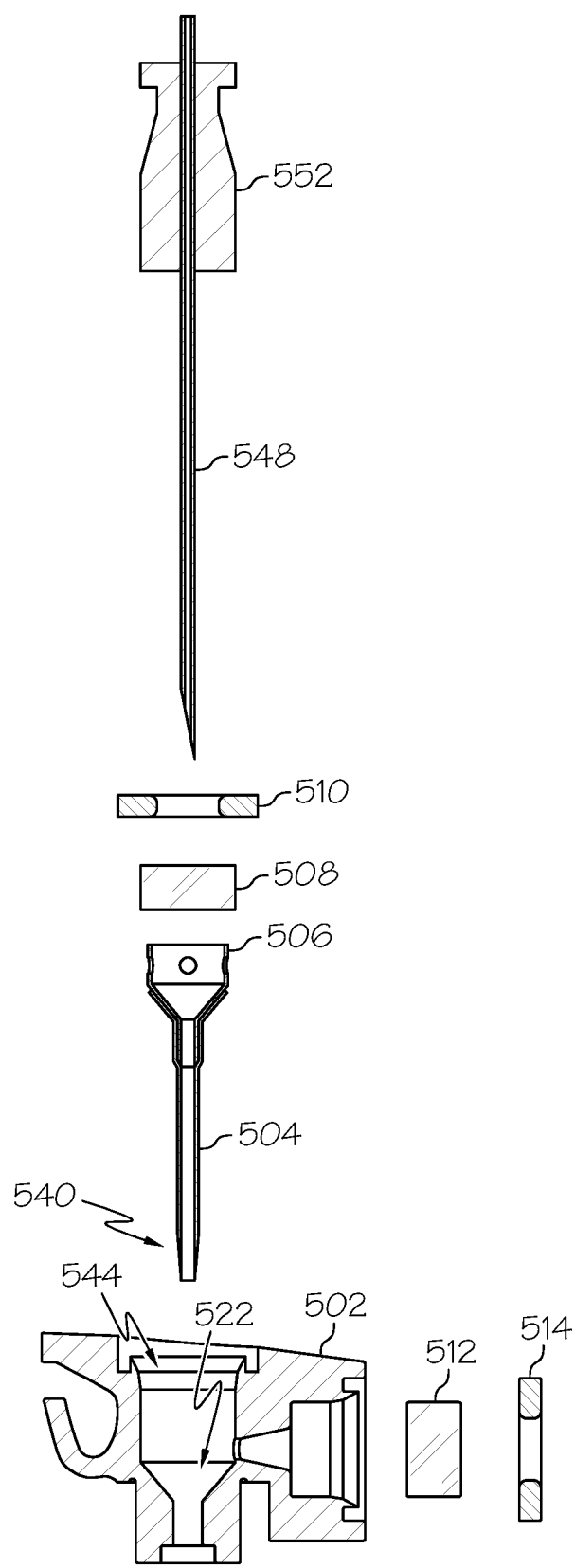
FIG. 22 is an exploded cross-sectional view of the assembly depicted in FIG. 21.

FIG. 19 is a perspective view of the fluid channel module 500, FIG. 20 is a perspective cross-sectional view of the fluid channel module 500, FIG. 21 is a cross-sectional view of the fluid channel module 500 (shown with a needle introducer component), and FIG. 22 is an exploded cross-sectional view of the assembly depicted in FIG. 21. This particular embodiment of the fluid channel module 500 includes, without limitation: a body section 502; a pliable cannula 504; a needle funnel 506; a first septum 508; a first septum cap 510; a second septum 512; and a second septum cap 514.

The external dimensions, features, and configuration of the body section 502 are similar (if not identical) to those found in the body section 402 of the fluid channel module 400. Indeed, the external dimensions, shape, and structure of the body section 502 are compatible with the universal coupling design of the infusion set component 200, as described above. Accordingly, the body section 502 includes an integrated snap hook 516, a retaining lip 518, and an output port 520 that facilitate coupling and attachment of the fluid channel module 500 into the base body section 300.

The outlet port 520 has a funnel-shaped internal opening 522 (see FIG. 22) that is shaped and sized to accommodate an end portion 524 of the pliable cannula 504 and a base section 526 of the needle funnel 506. FIG. 20 illustrates how the internal opening 522 is sized and contoured in accordance with the end portion 524 and the base section 526. When the fluid channel module 500 is installed into the base body section 300, the free end of the pliable cannula 504 extends from the outlet port 520 (as shown in FIG. 19).

Referring to FIG. 20, the fluid channel module 500 includes an interior fluid flow channel 530 formed and defined within the body section 502. The illustrated embodiment of the fluid flow channel 530 includes an inlet 532, a first segment 534, a main funnel zone 536, and an outlet 538. During fluid delivery operations, the fluid enters the inlet 532, flows through the first segment 534 and into the main funnel zone 536, and flows down the needle funnel 506 and into the pliable cannula 504. As described in more detail below, the fluid channel module 500 may include one or more seals, septa, or other elements that prevent leakage such that the fluid pressure generated during fluid delivery operations urges the fluid out of the pliable cannula 504.

The needle funnel 506 is located within the interior fluid flow channel 530, and it may serve as a retaining element for the pliable cannula 504. In this regard, the end portion 524 of the pliable cannula 504 receives the base section 526 of the needle funnel 506. This arrangement is desirable to hold and position the end portion 524 between the base section 526 of the needle funnel 506 and the funnel-shaped internal opening 522 (see FIG. 21). When the fluid channel module 500 is assembled as depicted in FIG. 20, the needle funnel 506 is urged toward the internal opening 522 to compress the end portion 524 of the pliable cannula 504 and form a seal with the body section 502. Thus, the end portion 524 serves as a seal to inhibit leakage of fluid from the outlet port 520.

The cannula 504 represents one suitable implementation of a fluid delivery conduit for the fluid channel module 500. The free end 540 of the cannula 504 represents the subcutaneous portion of the cannula 504 that serves to deliver the fluid to the patient. In contrast, the end portion 524 of the cannula 504 is located within the interior fluid flow channel 530. When the fluid channel module 500 is secured in the base body section 300, the cannula 504 passes through and extends from the hole 334. Thus, the cannula 504 protrudes from the bottom of the infusion set component 200, as shown in FIG. 2.

The septum 512 and the septum cap 514 are similar to their equivalents described above for the fluid channel module 400. The illustrated embodiment of the fluid channel module 500 also employs the additional septum 508 and the additional septum cap 510. The septum 508 is located and held in place in the body section 502 by the septum cap 510. The septum 508 applies downward pressure on the needle funnel 506 to retain the needle funnel 506 in place and to form a seal around the cannula 504. The septum 508 has a nominal non-pierced state where the septum 508 seals an introducer inlet 544 of the interior fluid flow channel 530. The non-pierced state of the septum 508 is shown in FIG. 20, and the introducer inlet 544 is shown in FIG. 22. In contrast, the septum 508 is pierced by an introducer needle 548 during an insertion procedure to insert the cannula 504 into the patient. When pierced, the septum 508 forms a seal around the introducer needle 548 during a priming operation (which introduces the fluid into the flow path, into the introducer needle 548, and into the cannula 504. FIG. 21 depicts the pierced state of the septum 508, and FIGS. 21 and 22 show the introducer needle 548.

Referring to FIG. 21 and FIG. 22, the introducer needle 548 is provided with a needle hub 552. Although not shown, the needle hub 552 is utilized with a suitably configured insertion device, mechanism, or component that is operated to insert the cannula 504 (and, in a combination infusion-sensor unit, the sensor 218) into the skin of the patient. The needle hub 552 is manipulated such that the introducer needle 548 passes through the center of the septum cap 510, pierces the septum 508, and is received by the needle funnel 506. The needle funnel 506 serves to guide the tip of the introducer needle 548 into the cannula 504 to accommodate insertion of the cannula 504 during an insertion procedure. The needle funnel 506 and the introducer needle 548 may be ported to allow the fluid to flow into the lumen of the cannula 504 during priming. In this regard, FIG. 20 depicts a number of port holes formed in the needle funnel 506, and FIG. 21 depicts a cutout formed in the outer wall of the introducer needle 548. The needle cutout serves as a port to allow the fluid to enter the introducer needle 548 during priming. After insertion, the needle hub 552 and the introducer needle 548 are retracted and removed from the fluid channel module 500, and the cannula 504 remains in its subcutaneous position. The septum 508 seals the introducer inlet 544 when the introducer needle 548 is removed from the fluid channel module 500.

As mentioned previously, the fluid channel module 500 is compatible with the universal coupling and attachment features of the base body section 300. Thus, the fluid channel module interface 330 of the base body section 300 can receive and maintain the fluid channel module 500 to form a cannula-based combined infusion-sensor unit if so desired to suit the needs of the patient. It should be appreciated that more than two different fluid channel module designs could be fabricated for compatibility with the base body section 300. The universal coupling features of the fluid channel module interface 330 allow a manufacturer to efficiently and effectively offer a variety of different infusion set configurations as needed to satisfy the needs of different patients, physicians, medical device providers, and caregivers.

Figure 23:
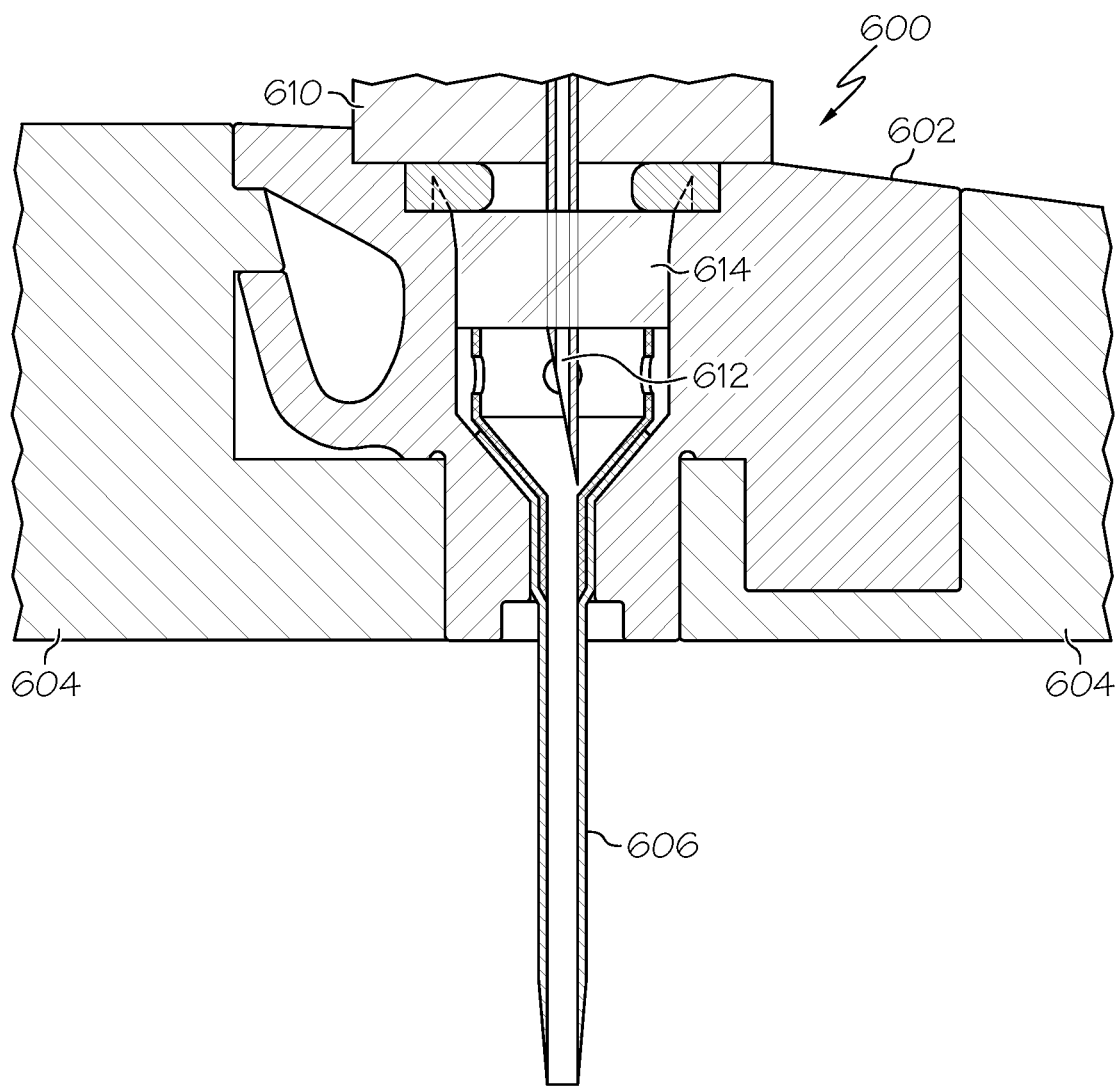
FIG. 23 is a cross-sectional view of an exemplary embodiment of a fluid infusion system that employs a top-entry fluid channel module.

Each of the fluid channel modules described above represents a side-entry component in that the needle of the fluid tubing connector enters the fluid channel module from the side (see, for example, FIG. 2 and FIG. 3). Alternative embodiments, however, could be designed to accommodate a fluid tubing connector that is coupled to the top of the fluid channel module. In this regard, FIG. 23 is a cross-sectional view of an exemplary embodiment of a fluid infusion system 600 that employs a top-entry fluid channel module 602. The fluid channel module 602 can be coupled to a compatible base body section 604 in the manner described above for the fluid channel module 400. It should be appreciated that FIG. 23 only depicts a portion of the base body section 604.

In contrast to the side-entry fluid channel modules, the fluid channel module 602 includes a vertically oriented fluid flow channel that leads to a fluid delivery cannula 606 (or, in alternative embodiments, a rigid needle). Accordingly, the fluid channel module 602 and the base body section 604 need not include any side ports or inlets. The fluid channel module 602 shares some features and elements with the fluid channel module 500. For the sake of brevity, common features, characteristics, and functional aspects will not be redundantly described here in the context of the fluid channel module 602.

The fluid infusion system 600 may also include a fluid tubing connector 610 (only a portion of which is depicted in FIG. 23). The fluid tubing connector 610 is coupled to the top of the fluid channel module 602 such that the connector needle 612 pierces the septum 614. As shown in FIG. 23, the end of the connector needle 612 is positioned such that fluid can be forced from the connector needle 612, into the fluid channel module 602, and out of the cannula 606 as needed. The septum 614 forms a fluid-tight seal around the connector needle 612 to minimize leakage. Moreover, the septum 614 is preferably designed to be self-sealing such that fluid does not leak when the fluid tubing connector 610 is removed from the fluid channel module 602.

Figure 24:
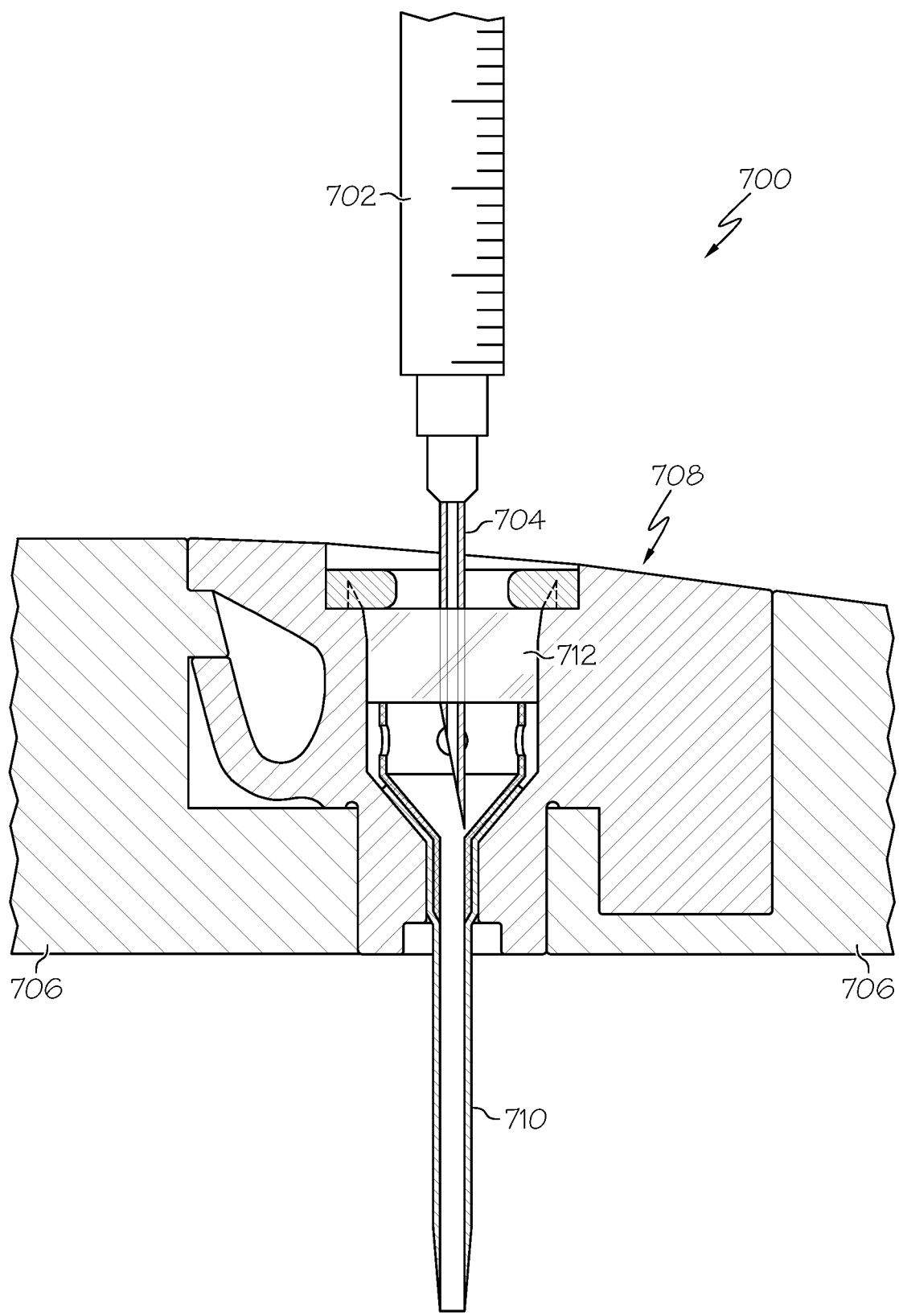
FIG. 24 is a cross-sectional view of an exemplary embodiment of a fluid infusion port system that employs a fluid channel module.

Each of the fluid channel modules described above cooperate with a fluid infusion device and an associated fluid tubing connector that physically and fluidly couples the fluid channel module to the fluid infusion device. As mentioned above with reference to FIG. 1, the fluid infusion device 102 regulates the amount of fluid delivered to the patient. In an alternative fluid delivery system, however, a fluid channel module having the features and characteristics described herein is utilized with an infusion port that accommodates delivery of fluid via a user-actuated device such as a syringe. In this regard, FIG. 24 is a cross-sectional view of an exemplary embodiment of a fluid infusion port system 700 that cooperates with, for example, a syringe 702 having a syringe needle 704.

The fluid infusion port system 700 generally includes, without limitation: a base 706 and a fluid channel module 708 coupled to the base 706. The fluid channel module 708 shares many features and characteristics with the fluid channel modules 400, 500, 602 described above. For the sake of brevity, common features, characteristics, and functional aspects will not be redundantly described here in the context of the fluid channel module 708.

The fluid infusion port system 700 is designed to be worn by the patient with a conduit 710 (e.g., a cannula as shown) inserted subcutaneously. When a bolus or dose of medication fluid is needed, the patient inserts the syringe needle 704 into the fluid channel module 708, and actuates the plunger of the syringe 702 to force the desired amount of fluid into the body via the conduit 710. More specifically, the syringe needle 704 (or any suitable fluid delivery needle) is inserted by piercing the septum 712, which normally covers and seals the inlet of the interior fluid flow channel defined within the fluid channel module 708. In practice, the syringe needle 704 is forced through the septum 712 and into the interior fluid flow channel such that fluid from the syringe 702 can be delivered to the interior fluid flow channel. The interior fluid flow channel and the conduit 710 cooperate to define and form a fluid flow path of the fluid infusion port system 700. When the syringe needle 704 is retracted and removed from the septum 712, the septum heals itself to seal the inlet.

It should be appreciated that various features and aspects of the other fluid channel modules described herein may also be incorporated for use with the fluid channel module 708 and the fluid infusion port system 700 if so desired. For example, the base 706 could be suitably configured to accommodate a sensor to sense an analyte of the patient (as described above with reference to FIG. 2). Moreover, the base 706 preferably includes universal or standardized coupling features for the fluid channel module 708. As mentioned above, the use of universal coupling features is desirable to allow a single design implementation of the base 706 to be compatible with a plurality of different fluid channel modules (e.g., modules having different conduit materials, conduit lengths, interior fluid flow channel configurations, etc.).

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A fluid channel module for an infusion set component of a fluid infusion device that delivers a fluid to a patient, the fluid channel module comprising:
   a body section comprising coupling features to mate with a base of the infusion set component;
   an interior fluid flow channel formed within the body section to receive the fluid from the fluid infusion device; and
   a conduit having a first end in fluid communication with the interior fluid flow channel, and having a second end to deliver the fluid to the patient, the conduit extending along an axial direction between the first and second ends;
   wherein the interior fluid flow channel has an inlet configured to receive a connector needle, and a channel segment coupling the inlet in fluid flow communication with the first end of the conduit, the channel segment extending in a lengthwise direction transverse to the axial direction of the conduit.

2. The fluid channel module of claim 1, wherein the body section is a unitary, one-piece component and the interior fluid flow channel is a passage formed integrally within the body section.

3. The fluid channel module of claim 1, wherein the conduit comprises a rigid hollow needle coupled to the body section in a fixed position.

4. The fluid channel module of claim 3, further comprising:
   an outlet port for the fluid flow channel; and
   a needle hub coupled around a section of the rigid hollow needle, wherein the needle hub is coupled to the outlet port to form a fluid seal with the outlet port, and wherein the needle hub secures the rigid hollow needle to the body section such that the first end is positioned within the interior fluid flow channel.

5. The fluid channel module of claim 4, further comprising a sealing element to form a fluid seal between the needle hub and the outlet port.

6. The fluid channel module of claim 1, further comprising a septum positioned at the inlet of the interior fluid flow channel, wherein:
   the septum is pierced by the connector needle of the fluid infusion device to facilitate delivery of the fluid from the fluid infusion device to the interior fluid flow channel when the connector needle is received by the inlet; and
   the septum seals the inlet when the connector needle is not received by the inlet.

7. An infusion set component for a fluid infusion device that delivers a fluid to a patient using either a first fluid channel module or a second fluid channel module, the infusion set component comprising:
   a base body section having first and second opposite-facing end portions;
   a fluid channel module interface formed in the first end portion of the base body section, the fluid channel module interface comprising first universal coupling features that mate with corresponding second universal coupling features of the first fluid channel module and with corresponding third universal coupling features of the second fluid channel module;
   a sensor interface formed in the base body section, wherein the sensor interface is configured to receive a sensor to facilitate sensing of an analyte of the patient; and
   a wireless sensor transmitter interface formed in the second end portion of the base body section, for mating with a wireless sensor transmitter and for electrically connecting the sensor with the wireless sensor transmitter when the sensor is received by the sensor interface and the wireless sensor transmitter is mated with the wireless sensor transmitter interface.

8. The infusion set component of claim 7, further comprising an attachment feature to accommodate removable coupling with a fluid tubing connector of the fluid infusion device.

9. The infusion set component of claim 8, wherein the attachment feature is integrally formed with the base body section.

10. The infusion set component of claim 7, further comprising a hole formed within the base body section, wherein the hole is universally shaped and sized to mate with a first port of the first fluid channel module, and to mate with a second port of the second fluid channel module.

11. The infusion set component of claim 7, further comprising a universal locking mechanism to lock either the first fluid channel module or the second fluid channel module in the fluid channel module interface.

12. The infusion set component of claim 7, wherein:
   the first fluid channel module comprises a rigid hollow needle to deliver fluid;
   the second fluid channel module comprises a pliable cannula to deliver fluid;
   the fluid channel module interface receives and maintains the first fluid channel module to form a needle-based combined infusion-sensor unit; and
   the fluid channel module interface receives and maintains the second fluid channel module to form a cannula-based combined infusion-sensor unit.

13. A fluid infusion port component to accommodate delivery of fluid to a patient, the fluid infusion port component comprising:
   a base; and
   a fluid channel module coupled to the base;
   the base comprising first universal coupling features that mate with corresponding second universal coupling features of the fluid channel module; and
   the fluid channel module comprising:
      an interior fluid flow channel having an inlet;
      a septum positioned at the inlet, wherein the septum is pierced by a fluid delivery needle to accommodate delivery of fluid into the interior fluid flow channel, and wherein the septum seals the inlet when the fluid delivery needle is removed from the septum; and
      a conduit in fluid communication with the interior fluid flow channel to deliver fluid from the interior fluid flow channel, the conduit extending along an axial direction;
      wherein the interior fluid flow channel includes a channel segment coupling the inlet in fluid flow communication with a first end of the conduit, the channel segment extending in a lengthwise direction transverse to the axial direction of the conduit.

14. The fluid infusion port component of claim 13, wherein the fluid channel module accommodates a user-actuated syringe.

15. The fluid infusion port component of claim 13, wherein the conduit is positioned within the fluid channel module opposite of the inlet.

16. The fluid channel module of claim 1, wherein the body section includes an interior zone in fluid communication with the channel segment, and wherein the interior zone has a lengthwise dimension that extends transverse to the lengthwise direction of the channel segment.

17. The fluid channel module of claim 16, wherein the lengthwise direction of the channel segment extends from the inlet to the interior zone of the body section.

18. The fluid channel module of claim 16, further comprising a septum located at the inlet of the interior fluid flow channel and wherein at least a portion of the channel segment extends from the septum to the interior zone of the body section.

19. The fluid channel module of claim 18, wherein the channel segment is open to the interior zone of the body section.

* * * * *